(12) United States Patent
Huang et al.

(10) Patent No.: US 7,045,366 B2
(45) Date of Patent: May 16, 2006

(54) PHOTOCROSSLINKED HYDROGEL BLEND SURFACE COATINGS

(75) Inventors: Wenxi Huang, Fremont, CA (US); Pil-je Um, Pittsburg, CA (US)

(73) Assignee: Ciphergen Biosystems, Inc., Fremont, CA (US)

(*) Notice: Subject to any disclaimer, the term of this patent is extended or adjusted under 35 U.S.C. 154(b) by 0 days.

(21) Appl. No.: 10/802,039

(22) Filed: Mar. 17, 2004

(65) Prior Publication Data

US 2005/0059086 A1  Mar. 17, 2005

Related U.S. Application Data

(63) Continuation-in-part of application No. 10/660,738, filed on Sep. 12, 2003.

(51) Int. Cl.
*G01N 33/544* (2006.01)
*C07C 221/00* (2006.01)

(52) U.S. Cl. ............... 436/529; 436/518; 436/528; 435/7.1; 435/287.1; 435/287.2; 564/305; 564/328; 564/315

(58) Field of Classification Search ............... 436/518, 436/528, 529, 161, 162, 173, 164; 435/7.1, 435/7.8, 283.1, 287.1, 287.2, 288.7; 422/50, 422/57; 564/305, 328; 522/46; 524/359
See application file for complete search history.

(56) References Cited

U.S. PATENT DOCUMENTS

| | | | |
|---|---|---|---|
| 4,381,239 A | 4/1983 | Chibata et al. | |
| 4,701,500 A | 10/1987 | Porath | |
| 5,075,371 A | 12/1991 | Boschetti et al. | |
| 5,118,937 A * | 6/1992 | Hillenkamp et al. | ........ 250/282 |
| 5,141,966 A | 8/1992 | Porath | |
| 5,185,313 A | 2/1993 | Porath | |
| 5,234,991 A | 8/1993 | Tayot et al. | |
| 5,268,097 A | 12/1993 | Girot et al. | |
| 5,563,056 A * | 10/1996 | Swan et al. | .................. 435/180 |
| 5,652,348 A | 7/1997 | Burton et al. | |
| 5,719,060 A | 2/1998 | Hutchens et al. | |
| 5,955,729 A * | 9/1999 | Nelson et al. | .............. 250/282 |
| 6,124,137 A | 9/2000 | Hutchens et al. | |
| 6,225,047 B1 | 5/2001 | Hutchens et al. | |
| 6,372,813 B1 * | 4/2002 | Johnson et al. | ............. 522/114 |
| 6,586,493 B1 * | 7/2003 | Massia et al. | ................. 522/87 |
| 2001/0045384 A1 | 11/2001 | Stipanovic et al. | |
| 2002/0055186 A1 * | 5/2002 | Barry et al. | ................. 436/518 |

(Continued)

FOREIGN PATENT DOCUMENTS

WO   WO 95/31279   11/1995

(Continued)

OTHER PUBLICATIONS

International Search Report of PCT/US2004/008210.

(Continued)

*Primary Examiner*—Bao-Thuy L. Nguyen
*Assistant Examiner*—Melanie J. Yu
(74) *Attorney, Agent, or Firm*—Foley & Lardner LLP

(57) ABSTRACT

Hydrogel polymer blends including precursors and crosslinked forms of the compositions. The blends provide an improved approach to achieve high quality, uniform coatings with better commercial viability than other approaches including copolymerization. Applications include mass spectral analysis of biomolecular analytes such as proteins. Dextran and acrylamide systems are preferred. Benzophenone groups can be used as photocrosslinking groups. Photoinitiators are not needed. Functionalities which can selectively bind to biomolecular analytes are included.

20 Claims, 15 Drawing Sheets

LIGAND FUNCTIONALIZED DEXTRAN

PHOTO-LINKER MODIFIED DEXTRAN

BLEND

UN-MODIFIED DEXTRAN

FLUORESCENT LABELLED-DEXTRAN

U.S. PATENT DOCUMENTS

2003/0008971 A1* 1/2003 Won et al. ................. 525/54.2
2003/0218130 A1* 11/2003 Boschetti et al. ........... 250/288
2004/0029191 A1* 2/2004 Lomas et al. ................ 435/7.9

FOREIGN PATENT DOCUMENTS

WO    WO 96/00735    1/1996
WO    WO 03/064594    8/2003

OTHER PUBLICATIONS

G. H. Scholz et al., "Salt-independent Binding of Antibodies from Human Serum to Thiophilic Heterocyclic Ligands", Journal of Chromatography B., 1998, pp. 189-196, vol. 709.

S. C. Burton et al., "Hydrophobic Charge Induction Chromatography: Salt Independent Protein Adsorption and Facile elution with Aqueous Buffers", Journal of Chromatography a, 1998, pp. 71-81, vol. 814.

L. Guerrier et al., "New Methods for the Selective Capture of Antibodies Under Physiological Conditions", Bioseparation, 2000, pp. 211-221, vol. 9.

E. Boschetti, "The Use of Thiophilic Chromatography for Antibody Purification: A Review", J. Biochem. Biophys. Methods, 2001, pp. 361-389, vol. 49.

Bo-Lennart Johansson et al., "Preparation and Characterization of Prototypes for Multi-Modal Separation Media Aimed for Capture of Negatively Charged Biomolecules at High Salt Conditions", Journal of Chromatography A, 2003, pp. 21-33, vol. 1016.

Bo-Lennart Johansson et al., "Preparation and Characterization of Prototypes for Multi-Modal Separation Aimed for Capture of Positively Charged Biomolecules at High-Salt Conditions", Journal of Chromatography A, 2003, pp. 35-49, vol. 1016.

* cited by examiner

BARE SUBSTRATE

MEP GEL COATED

PHOTOCROSSLINKED HYDROGEL BLEND SURFACE COATINGS

RELATED APPLICATIONS

This application is a continuation-in-part application and claims priority back to Ser. No. 10/660,738 filed Sep. 12, 2003, the complete disclosure of which is hereby incorporated by reference.

BACKGROUND

The term "hydrogel" generally connotes a hydrophilic, crosslinked, organic polymeric material (i.e., hydrophilic polymer networks) that swells in and retains water (see, e.g., WO00/66265 and U.S. Pat. No. 6,613,234 (Voute) to Ciphergen Biosystems). Hydrogels have a variety of commercial applications, illustrated by their use in contact lens, sensors, tissue adhesives, drug delivery, dressings, and surface coatings. For example, see U.S. Pat. No. 6,017,577 to Hostettler et al. In particular, hydrogel surface coatings are used in biomedical devices, such as catheters, catheter balloons, and stents, as illustrated by U.S. Pat. No. 5,601,538 to Deem. Hydrogels can be applied as continuous layers or as patterns of discreet regions on a surface (e.g., gel "patches" or "pads").

The distinctive ability of hydrogels to swell extensively in water, forming a structurally stable but liquid-compatible structure, arises from their lightly crosslinked character, which in turn arises from how they are made. One approach to such manufacture is by photopolymerization and photocrosslinking, respectively, as disclosed in U.S. Pat. No. 5,567,435 and No. 6,156,478. Thus, the '478 patent describes photocrosslinkable and photopatternable hydrogel compositions that are based on an azlactone-functional monomer. These hydrogels can be patterned onto a substrate by means of a photomask or laser-induced thermal imaging, and the azlactone functionality can be used to bind biomolecules to the substrate. According to the '478 patent, the described hydrogel compositions can be used to produce a "microchip," such as a low- or high-density DNA chip or a microarray of enzyme-containing gel pads.

Another approach to producing hydrogel materials is by deposition of a monomer solution on the substrate surface and in situ polymerization and crosslinking of monomer mixture using a thermal or photoinitiator, as disclosed in PCT application WO 00/66265. Changing the amount of monomer and cross-linker can affect the thickness and pore size of the resulting hydrogel layers.

U.S. Pat. Nos. 5,512,329 and 5,002,582 to Guire et al. discloses polymers which have latent reactive groups for covalent bonding to substrate surfaces. These polymers covalently bond to the substrate surface when the latent reactive groups are stimulated by an external stimulus such as actinic radiation. These polymers, however, are generally designed for repelling protein rather than adsorbing proteins, or selectively interacting with and binding of proteins with tailored control of functional group chemistry. Moreover, these polymers are not prepared by controlled copolymerization methods which allow for suitable hydrogel formation and suitable chemical binding selectivity with proteins and other biomolecules.

Despite their demonstrated versatility and applicability in certain contexts, the potential of hydrogels has not been fully exploited in biochip-based methods of protein detection, in particular, mass-spectral techniques, such as Matrix-Assisted Laser Desorption/Ionization (MALDI) and Surface-Enhanced Laser Desorption/Ionization (SELDI) mass spectroscopy, which are of increasing popularity for protein analysis. Moreover, conventional procedures for producing hydrogels typically do not provide the coating uniformity and homogeneity that would facilitate MALDI or SELDI mass spectroscopy. For example, using in situ polymerization of monomer mixture do not typically provide controlled polymerization processes. The polymerization and surface attachment typically take place simultaneously on an individual spot, and each spot represents a separated reactor. The resulting hydrogel materials can suffer from spot-to-spot and chip-to-chip variations. The conventional procedures also typically do not provide a three-dimensional polymeric structure that has sufficient surface area, controllable porosity and ligand density for capturing proteins and biomolecules in a broad range of molecular weight. The hydrogels having sufficient surface area can provide a probe with high binding capacity and sensitivity, which is attractive when the amount of the sample available for analysis is very small and limited. The hydrogels having controllable pore size and/or ligand density can provide a probe with desirable selectivity and binding capacity that meet the demands of specific biological applications. Also, conventional methods typically do not provide the coating uniformity and homogeneity that would facilitate MALDI or SELDI mass spectroscopy. For instance, uniformity in the hydrogel surface coating may provide a more accurate time-of-flight analysis of samples, as all analytes absorbed on the probe surface are equidistant from an energy source of a gas phase ion spectrometer. Also, conventional formulations for probe materials may not be compatible with desired process methods such as spin coating, dip coating, photopatterning, or useful combinations thereof. The presence of low molecular weight components can cause problems. For instance, see PCT application WO 00/66265 and U.S. patent publication 20020060290 A1. Other literature includes U.S. Pat. No. 6,579,719 (Hutchens), U.S. Pat. No. 6,610,630 (Schwarz), and U.S. Pat. No. 6,675,104 (Paulse).

A need exists to improve biochip methods of detecting biomolecules, such as proteins, including detection by MALDI, SELDI, and other mass-spectrometric analyses through use of probe materials characterized by greater uniformity and structural stability, through better control of coating thickness, hydrogel porosity, and spot variation. Advantages which the present invention provides include maximizing the value of a hydrogel surface for SELDI and MALDI analysis including but not limited to the following factors: (1) complete coverage of the hydrogel, (2) control of hydrogel thickness and swelling degree, (3) uniformity of hydrogel coatings, (4) stability of hydrogel on the surface, (5) controlling the density of the selective binding functionality, (6) ease and consistency of producing hydrogel, and (7) substantially absence of low molecular weight components which can diffuse out and interfere with the analyses by generating signal noise.

Hydrogel blends are known including blends described in U.S. Pat. No. 6,586,493 (Massia), U.S. Pat. No. 6,211,296 (Frate), and U.S. Pat. No. 4,693,887 (Shah). Hydrogel blends, however, are not generally developed for use in mass spectral methods such as, for example, SELDI and MALDI. A need exists to improve the control over the hydrogel system including improved processability, synthetic versatility, economics, and convenience. Challenges exist however because at times the presence of one useful functional group in a hydrogel system can interfere with use of and synthetic strategies for another functional group.

SUMMARY

Several non-limiting aspects of the present invention are summarized in this section. The present invention demonstrates among other things that, for a hydrogel system, blending provides a useful tool to provide independent control of synthetic chemical reactions needed to prepare useful hydrogel blends which other tools such as copolymerization have more difficulty providing. Preparation of blends allows the use of a limited number of feedstock polymers to be used to prepare a wide variety of materials, which shortens research and development time and the amount of synthetic labor needed. Moreover, better control over polymer properties can be achieved.

In a first embodiment, the present invention provides a hydrogel polymer blend composition prepared by crosslinking a hydrogel polymer blend precursor composition comprising: (a) a first polymer comprising a photocrosslinkable functionality, wherein the first polymer optionally also comprises functionality for selectively binding a biomolecular analyte, and (b) a second polymer comprising functionality for selectively binding a biomolecular analyte, wherein the functionality for selective binding a biomolecular analyte in the first polymer and the second polymer can be the same or different, and wherein the amounts of the first and second polymers, and the amounts of the photocrosslinking functionality and the functionality for selective binding a biomolecular analyte provide the hydrogel precursor polymer blend composition with, respectively, the ability to be photocrosslinked into the hydrogel and the ability of the hydrogel to selectively bind to the biomolecular analyte. In a preferred embodiment, the functionality for selective binding a biomolecular analyte in the first polymer is present and can be the same as the functionality for selective binding a biomolecular analyte in the second polymer. In a preferred embodiment, the first polymer can comprise a linear polymer backbone having side groups that comprise photocrosslinkable functionality, and the second polymer comprises a linear polymer backbone having side groups that comprise the functionality for selectively binding a biomolecular analyte. In a preferred embodiments, the functionality for selective binding can be effective for covalent bonding or non-covalent bonding with the biomolecular analyte. In addition, the functionality for selective binding can be a chromatographic or biospecific binding functionality. The hydrogel composition can, if desired, further include energy absorbing moieties or one or more fluorescent groups. Preferably, the hydrogel composition is substantially free of photoinitiator.

In a second embodiment, the present invention also provides a hydrogel polymer blend composition prepared by: (A) crosslinking a hydrogel polymer blend precursor composition comprising: (i) a first polymer comprising a photocrosslinkable functionality, wherein the first polymer optionally also comprises functionality for selectively binding a biomolecular analyte, and (ii) a second polymer which can be synthetically modified to comprise functionality for selectively binding a biomolecular analyte, whereby a crosslinked hydrogel is formed; (B) synthetically modifying the crosslinked hydrogel so it comprises functionality for selective binding to a biomolecular analyte, wherein the amounts of the first and second polymers, and the amounts of the photocrosslinkable functionality and the functionality for selective binding, provide the hydrogel precursor polymer blend with the ability to be photocrosslinked into a hydrogel and the hydrogel to be selectively bind to the biomolecular analyte.

A third embodiment is a substrate that comprises a substrate surface and a hydrogel polymer blend composition thereon, wherein the composition comprises (i) a first polymer comprising crosslinked functionality, wherein the first polymer optionally also comprises functionality for selectively binding a biomolecular analyte, and (ii) a second polymer comprising functionality for selectively binding a biomolecular analyte, which can be the same or different as the functionality for selective binding a biomolecular analyte for the first polymer.

Also provided in a fourth embodiment is a method for functionalizing a surface with a hydrogel composition comprising: (A) providing (i) a substrate presenting a surface, and (ii) a hydrogel blend precursor composition according to the first and second embodiments described above in this summary section, (B) contacting the precursor composition according to the first and second embodiments described above in this summary section to form a layer of the composition on the surface, (C) crosslinking at least some of the composition on the surface to form hydrogel in contact with the surface.

Other embodiments include a method of making the hydrogel blend precursor composition according to the first and second embodiments described above in this summary comprising the step of mixing the first and second polymers to form the hydrogel precursor polymer blend.

Moreover, the invention provides a particle comprising the hydrogel according to crosslinked forms of the hydrogel compositions for the first and second embodiments described above in this summary section.

Still further, the invention provides a method for detecting a biomolecular analyte comprising: (i) contacting the substrate according to the third embodiment described above in this summary section with a sample that contains a biomolecular analyte and then (ii) detecting the biomolecular analyte by virtue of its binding the functionality for selective binding.

The invention also provides a hydrogel polymer blend composition comprising: (a) a first polymer comprising a photocrosslinked functionality, and (b) a second polymer comprising (i) one or more functionalities for selectively binding a biomolecular analyte by non-covalent binding, (ii) one or more functionalities for selectively binding a biomolecular analyte by covalent binding, (iii) one or more energy absorbing moieties, or combinations thereof. In a preferred embodiment, the second polymer comprises (i) one or more functionalities for selectively binding a biomolecular analyte by non-covalent binding. In another preferred embodiment, the second polymer comprises (ii) one or more functionalities for selectively binding a biomolecular analyte by covalent binding. In another preferred embodiment, the second polymer comprises (iii) one or more energy absorbing moieties. In this embodiment, the second polymer does not necessarily have the functionality for selectively binding a biomolecular analyte, whether covalent or non-covalent binding. In this embodiment, the first polymer also can comprise if desired the functionality for selective binding, be it covalent or non-covalent binding, or the energy absorbing moiety. The amounts of the first and second polymers and the amounts of the functionality for selective binding and energy absorbing moieties can be controlled for a particular application so that a useful hydrogel is formed.

The invention also provides a hydrogel polymer blend composition prepared by crosslinking a hydrogel polymer blend precursor composition comprising: (a) a first polymer comprising a photocrosslinkable functionality, wherein the first polymer optionally also comprises functionality for selectively binding a biomolecular analyte, and (b) a second polymer comprising an energy absorbing functionality, and wherein the amounts of the first and second polymers, and the amounts of the photocrosslinking functionality and the energy absorbing functionality provide the hydrogel precursor polymer blend composition with, respectively, the ability to be photocrosslinked into the hydrogel and the ability of the hydrogel to promote desorption of associated analytes into the gas phase when struck by a high energy source such as a laser.

The invention also provides a hydrogel polymer blend composition prepared by crosslinking a hydrogel polymer blend precursor composition comprising: (a) a first polymer comprising a photocrosslinkable functionality, wherein the first polymer optionally also comprises functionality for selectively binding a biomolecular analyte, and (b) a second polymer, and wherein the hydrogel further comprises reactive groups capable of forming a covalent bond with a biomolecule and wherein the amounts of the first and second polymers, and the amounts of the photocrosslinking functionality and the energy absorbing functionality provide the hydrogel precursor polymer blend composition with the ability to be photocrosslinked into the hydrogel.

Also provided is a hydrogel coating kit comprising: (a) a first composition comprising a first polymer comprising a photocrosslinkable functionality, wherein the first polymer optionally also comprises functionality for selectively binding a biomolecular analyte, and (b) a second composition comprising a second polymer comprising (i) functionality for selectively binding a biomolecular analyte, wherein the functionality for selective binding a biomolecular analyte in the first polymer and the second polymer can be the same or different, or (ii) one or more energy absorbing moieties.

Another hydrogel coating kit comprises: (a) a first composition comprising a first polymer comprising a photocrosslinkable functionality, wherein the first polymer optionally also comprises functionality for selectively binding a biomolecular analyte, and (b) a second composition comprising a second polymer which can be synthetically modified to comprise functionality for selectively binding a biomolecular analyte.

Additional non-limiting basic and novel features of the present invention include, without limitation, that photoinitiators are not needed as a separate ingredient. Moreover, crosslinking reactions occur on polymer molecules even when that polymer molecule may not have a photocrosslinkable group. For example, a benzophenone group can abstract many C—H bonds. Many crosslinking reactions require that reaction occur by radical polymerization from an unsaturated group like acrylate or methacrylate attached along a polymer backbone or by photodimerization.

DETAILED DESCRIPTION

I. Introduction

Figure 1:
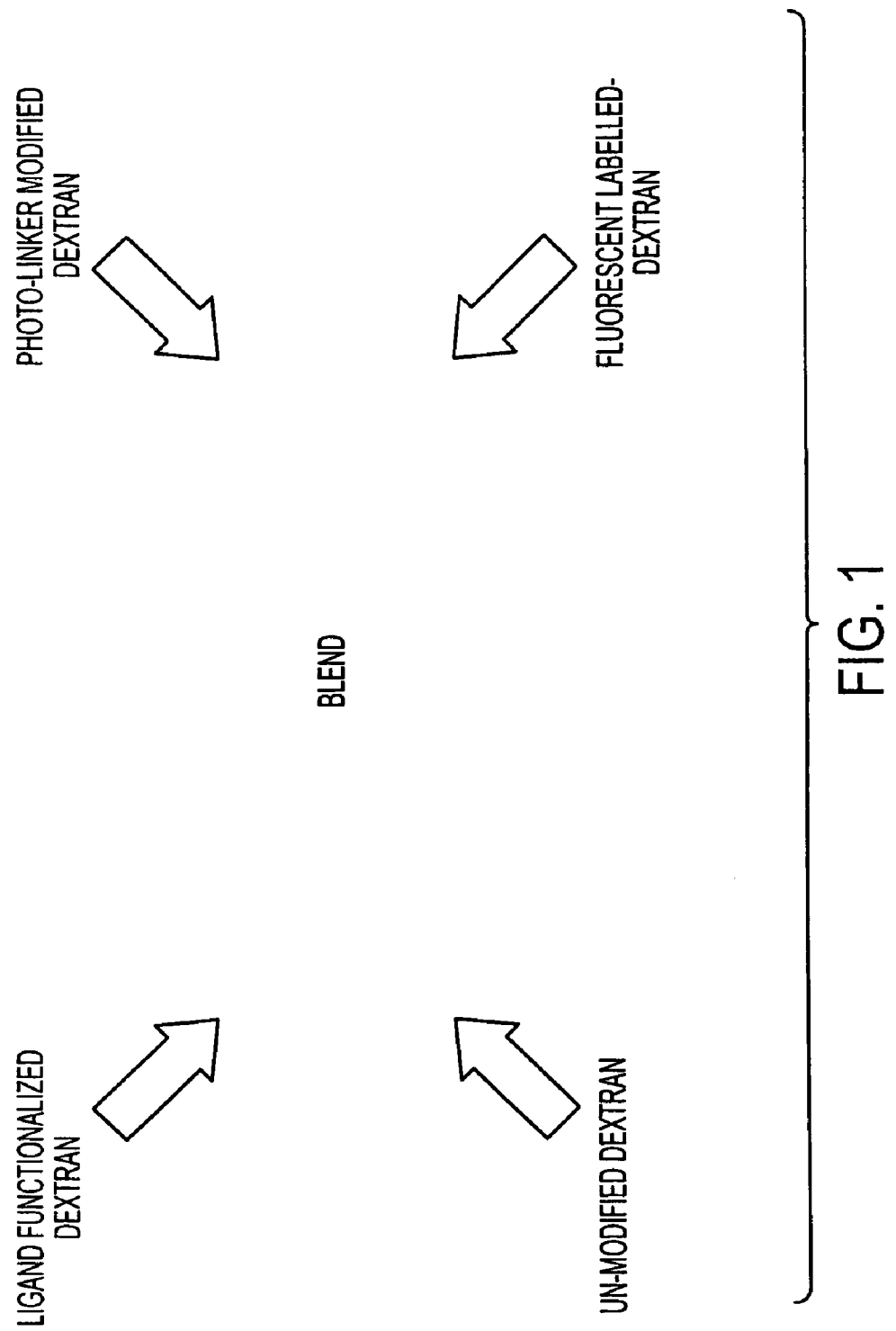
FIG. 1. Schematic of Polymer Blending Approach.

In this application, which describes among other things improved materials and methods for hydrogels and uses in proteomics and mass spectroscopy, the following terms are used:

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" ("SEAC") or "affinity gas phase ion spectrometry" (e.g., "affinity mass spectrometry") is a version of the SELDI method that uses a probe comprising an absorbent surface (a "SEAC probe"). "Adsorbent surface" refers to a sample presenting surface of a probe to which an adsorbent (also called a "capture reagent" or an "affinity reagent") is attached. An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates (e.g., Cu, Fe, Ni, Zn, Gallium), hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. An adsorbent is "bioselective" for an analyte if it binds the analyte with an affinity of at least $10^{-8}$ M, $10^{-9}$ M, $10^{-10}$ M, $10^{-11}$ M or $10^{-12}$ M. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

In a preferred embodiment affinity mass spectrometry involves applying a liquid sample comprising an analyte to the adsorbent surface of a SELDI probe. Analytes, such as polypeptides, having affinity for the adsorbent bind to the probe surface. Typically, the surface is then washed to remove unbound molecules, and leaving retained molecules. The extent of analyte retention is a function of the stringency of the wash used. An energy absorbing material (e.g., matrix) is then applied to the adsorbent surface. Retained molecules are then detected by laser desorption/ionization mass spectrometry.

SELDI is useful for protein profiling, in which proteins in a sample are detected using one or several different SELDI surfaces. In turn, protein profiling is useful for difference mapping, in which the protein profiles of different samples are compared to detect differences in protein expression between the samples.

"Surface-Enhanced Neat Desorption" or "SEND" is a version of SELDI that involves the use of probes ("SEND probe") comprising a layer of energy absorbing molecules attached to the probe surface. Attachment can be, for example, by covalent or non-covalent chemical bonds. Unlike traditional MALDI, the analyte in SEND is not required to be trapped within a crystalline matrix of energy absorbing molecules for desorption/ionization. "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-methoxy)silyl propyl methacrylate. In another embodiment, the composition is a co-polymer comprising α-cyano-4-methacryloyloxycinnamic acid and octadecylmethacrylate ("C18 SEND"). SEND is further described in U.S. Pat. No. 5,719,060 and WO 03/64594 (Kitagawa, "Monomers And Polymers Having Energy Absorbing Moieties Of Use In Desorption/Ionization Of Analytes", Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and desorption without the need to apply external matrix. The C18 SEND biochip is a version of SEAC/SEND, comprising a C18 moiety which functions as a capture reagent, and a CHCA moiety which functions as an energy absorbing moiety.

"Surface-Enhanced Photolabile Attachment and Release" or "SEPAR" is a version of SELDI that involves the use of probes having moieties attached to the surface that can covalently bind an analyte, and then release the analyte through breaking a photolabile bond in the moiety after exposure to light, e.g., laser light. SEPAR is further described in U.S. Pat. No. 5,719,060.

"Adsorption" refers to detectable non-covalent binding of an analyte to an adsorbent or capture reagent.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

"Biochip" refers to a solid substrate having a generally planar surface to which a capture reagent (adsorbent) is attached. Frequently, the surface of the biochip comprises a plurality of addressable locations, each of which location has the capture reagent bound there. Biochips can be adapted to engage a probe interface and, therefore, function as probes.

Introduction to Hydrogel Blends

The present invention generally relates to hydrogel blends, and hydrogels and blends are generally known in the polymer art. See, for example, (1) *Contemporary Polymer Chemistry*, Allcock and Lamp, Prentice Hall, 1981, and (2) *Textbook of Polymer Science*, $3^{rd}$ Ed., Billmeyer, Wiley-Interscience, 1984.

In the present invention, polymer blends can be prepared by mixing two or more polymers together including binary and ternary blends. In some cases, lower molecular weight polymers or oligomers can be used but, generally, higher molecular weight, film-forming, self-supporting polymers are preferred for preparing blends. Blends can be formulated in the present invention to provide high quality thin films or layers. The polymers can be in a variety of forms including, for example, homopolymers, copolymers, crosslinked polymers, network polymers, short chain or long chain branched polymers, interpenetrating polymer networks, and other types of mixed systems known in the polymer art. The polymer blends can swell when exposed to aqueous environments and form hydrogel states characterized by pore size and high water content. Hydrogels for use in mass spectral applications are described in, for example, US patent application publication 2003/0218130 filed Apr. 14, 2003 to Boschetti et al. which in particular describes a series of polysaccharide-based, in particular, dextran-based materials, including interpenetrating networks, and claims priority to provisional application Ser. No. 60/376,837 filed May 2, 2002, both of which are hereby incorporated by reference in their entirety.

One polymer of the blend comprises a photocrosslinkable functionality that can be used to cross-link the polymer with the other polymer and with itself. Another polymer comprises a functional group that can fall into one of several classes. One class is a binding functionality. A binding functionality can include groups for non-covalently binding an analyte, such as a chromatographic adsorbent or a biospecific adsorbent. The binding functionality also can have means for covalently binding a molecule that, in turn, can bind an analyte. For example, an epoxide or imidizole can bind a protein that, in turn, can bind another protein or a small molecule such as a drug. Another class is an energy absorbing functionality. Energy absorbing functionalities have preferential absorbance at wavelengths of energy sources used in laser desorption/ionization procedures. As such, they promote the desorption and ionization of analytes into the gas phase in laser desorption methods. In certain embodiments, the blended polymer can comprise both binding and energy absorbing functionalities on one or more polymers in the blend.

More specifically, this invention contemplates the following cross-linked hydrogels. In one embodiment, the hydrogel is the product of cross-linking between a first polymer comprising photoreactive moieties, such as benzophenone, that can engage in the cross-linking reaction, and a second polymer comprising moieties that engage in non-covalent binding with an analyte, such as a chromatographic adsorbent or a biospecific adsorbent. In another embodiment, the hydrogel is the product of cross-linking between a first polymer comprising photoreactive moieties and a second polymer comprising energy absorbing moieties that can absorb light from a high energy source, such as a laser, and promote desorption of an analyte molecule associated with hydrogel into the gas phase. In another embodiment the hydrogel is the product of cross-linking between a first polymer comprising photoreactive moieties and a second polymer that does not comprise a photoreactive group, wherein the hydrogel is derivatized, after cross-linking, with one or more of an adsorbent functionality, an energy absorbing functionality or a reactive functionality, such as epoxide or imidizole, that can covalently couple a biomolecule, such as a protein, that itself may be used to bind analyte molecules. In further embodiments these hydrogels coat at least a portion of the surface of a substrate, such as a biochip.

FIG. 1 provides an overview of the blending strategy provided by the present invention. FIG. 1 describes a preferred embodiment using dextran-based materials but the invention is not limited to dextran materials. In FIG. 1, the "photo-linker modified dextran" is an embodiment for the first polymer described further below based on photocrosslinkable functionality, and the "ligand functionalized dextran" is an embodiment for the second polymer described further below based on a functionality which can selectively bind a biomolecular analyte. FIG. 1 further illustrates additional components which can be an unmodified polymer such as, for example, unmodified dextran and labeled polymer which can be, for example, fluorescently labeled dextran. The unmodified polymer can be used for, for example, a diluent of the ligand functionalized dextran and/or the photocrosslinker modified dextran so that the ligand and/or the crosslinker density can be controlled. The fluorescently labeled dextran can be used in, for example, double detection quality control.

The present blends can comprise monomeric subunits that comprise a photocrosslinkable functionality, which have been previously described in PCT application serial no. PCT/US04/04887 filed Feb. 20, 2004 , which is hereby incorporated by reference in its entirety. The present blends can also comprise monomeric subunits that comprise a selective binding functionality, which also have been previously described in PCT application serial no. PCT/US04/04887 filed Feb. 20, 2004, which is hereby incorporated by reference in its entirety.

An embodiment for a hydrogel blend was also described in prior U.S. patent application Ser. No. 10/660,738 filed Sep. 12, 2003 ("Preparation and Use of Mixed Mode Solid Substrates for Chromatography Adsorbents and Biochip Arrays"), the complete disclosure of which is incorporated herein by reference and relied upon. In this '738 patent application, a solid support is described which can be modified with a covalently coated layer such as, for example, a silyl layer, which in turn covalently binds a cross-linked polysaccharide. As shown in Example 10 of the '738 patent application, the polysaccharide is preferably a blend of two polysaccharides, including a first polysaccharide and a second polysaccharide that is substituted with one or more crosslinking groups. Preferably, according to the '738 application, the polysaccharides in this regard include dextran, hydroxyethylcellulose, starch, amylase, and agarose, and most preferably dextran. Suitable crosslinking agents include but are not limited to benzophenone groups. Upon crosslinking, according to the '738 patent application, the polysaccharides crosslink and also covalently attach to the support. In the present specification, hydrogel blends are further described including mixtures of a first and second polymer.

Sub-Embodiment A

One sub-embodiment (Embodiment A) comprises the subject matter of the appended claims, including equivalents thereof, which is novel over the particular disclosure of the '738 patent application. In this sub-embodiment A, the particular subject matter of the '738 patent application including the description of the polysaccharide-based hydrogel blend is excluded.

II. First Polymer: Photocrosslinkable Polymer

The invention provides a first polymer comprising a photocrosslinkable functionality, wherein the first polymer optionally also comprises functionality for selectively binding a biomolecular analyte. The first polymer can be prepared by homopolymerizing or copolymerizing one or more monomers. For example, the first polymer can be prepared by copolymerizing monomers to form a copolymer comprising photocrosslinkable functionality and functionality for selective binding a biomolecular analyte. The first polymer can be, for example, a photocrosslinkable polymer as described in for example PCT patent application (US designated) serial no. PCT/US04/04887 filed Feb. 20, 2004, which is hereby incorporated by reference in its entirety. This PCT application describes use of copolymerization to control the amount and density of photocrosslinkable groups in the copolymer and in the final hydrogel precursor, which controls the crosslink density in the final hydrogel. It also describes a variety of biomolecular analytes. In the present invention, however, a single polymer or copolymer can be used in combination with various amounts of second polymer to control the amount and density of the photocrosslinkable groups in the hydrogel precursor and the crosslink density in the final hydrogel.

The first polymer can also be prepared as described in the PCT application PCT/US04/04887 by modifying an existing polymer, a first pre-functionalized polymer, with photocrosslinking groups by, for example, covalently coupling the groups to the side groups of a polymer chain to introduce the photocrosslinkable functionality. This embodiment is particularly of interest for preparing nonionic polysaccharide based hydrogels including dextran hydrogels.

The first polymer can comprise functionality which binds biomolecular analyte as well but that is not required. Rather, the second polymer can provide the binding functionality. When selective binding groups are present in the first polymer, they can be the same as or different from the selective binding groups of the second polymer. Mixed-modes of operation can be used.

The structural type of the polymeric hydrogel precursor generally, including the first and second polymers, and the type of polymeric backbone is not particularly limited but can be, for example, a linear polymer, a branched polymer, or even a dendritic polymer. Preferably, its linear. Although the polymeric hydrogel precursor, including the first and second polymer, is not generally crosslinked prior to conversion to the hydrogel under photocrosslinking conditions, it nevertheless may be in some cases water-swellable only and not water soluble. In other words, the polymeric hydrogel precursor, including first and/or second polymer, can be water-soluble or water-swellable. Monomers and prepolymers can be used which are known in the art to provide hydrogels. Preferably, the polymeric hydrogel precursor comprises a linear polymeric backbone that is comprised of carbon and that carries first side groups having the photocrosslinkable functionality and, optionally, second side groups having the selective binding functionality.

The polymeric hydrogel precursor, including the first polymer, can be prepared by a variety of synthetic methods which are not particularly limited. Upon synthesis, the polymeric hydrogel precursor can be a polymer chain having a polymeric backbone and at least two kinds of functionality covalently bound to the polymer backbone: photocrosslinkable functionality and functionalities which can selectively bind. Selective binding functionalities are able to select preferentially a target based on chemical interactions known in the art including, for example, covalent binding, non-covalent binding, electrostatic binding, and other modes described further herein. These functionalities can be regularly or randomly distributed along the polymeric backbone. Random distribution can help improve uniformity in the polymeric material, which can aid in the accuracy of the mass spectroscopic applications such as SELDI. Upon crosslinking of the hydrogel, the selective binding functionalities can selectively react with proteins and other biomolecular analytes and targets including covalent and non-covalent binding reaction.

In preferred embodiments, the polymeric hydrogel precursor, including first and second polymer, is a polysaccharide, e.g., dextran, or polyolefin composition. In a preferred embodiment, the polymeric hydrogel precursor, including first and second polymer, comprises a linear, carbon backbone represented by monomeric subunits:

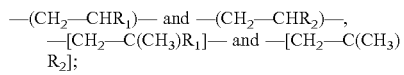

—(CH$_2$—CHR$_1$)— and —(CH$_2$—CHR$_2$)—,
—[CH$_2$—C(CH$_3$)R$_1$]— and —[CH$_2$—C(CH$_3$)R$_2$];

wherein R$_1$ and R$_2$ comprise the groups with the photocrosslinkable and selective binding functionalities, respectively. In general, monomers provide either the photocrosslinkable functionality or the selective binding functionalities. However, other monomers can be present in the polymeric hydrogel precursor as well. The presence of these monomers can be used to control the density of binding functionalities desired in the polymer composition. Suitable selection of monomers can provide the resulting polymeric hydrogel precursor with improved water-solubility, biocompatibility, and with reduced non-specific absorption. Preferred monomers provide an optimal combination of such properties.

The polymeric hydrogel precursor, in preferred embodiments for the first polymer, consists essentially of a linear copolymeric backbone having side groups that comprise the photocrosslinkable functionality and the selective binding functionality, wherein other structural units in the copolymer do not interfere with the ability to be photocrosslinked and, upon crosslinking, to selectively react with protein under aqueous conditions. In general, the copolymer structure is designed to bind selectively proteins, not repel proteins.

The first monomeric subunits that comprise a photocrosslinkable functionality are not particularly limited. These first monomeric subunits can function as a photoinitiator in a photocrosslinkable polymeric composition. In other words, because of these monomer subunits, photoinitiator does not need to be, and preferably is not, added to the composition for photocrosslinking. For example, the photocrosslinkable functionality can be a UV-curable functionality. The photocrosslinkable functionality is sufficiently sensitive to photons that it becomes highly reactive when exposed to photocrosslinking conditions so that a photoinitiator is not needed to generate photocrosslinking. For example, the photocrosslinkable functionality can be capable of hydrogen abstraction reactions when exposed to photocrosslinking conditions. Examples of photocrosslinkable functionalities include benzophenone, diazo ester, aryl azide, and diazirine, including derivatives thereof such as benzophenone derivatives. Hydrogen abstraction chemistry for benzophenone type compounds is disclosed, for example, in U.S. Pat. No. 5,856,066. Additional photocrosslinkable functionalities, or so-called "latent reactive groups," are described in for example U.S. Pat. No. 5,002,582.

In a preferred embodiment, the photocrosslinkable functionality is a ketone functionality, or an organic carbonyl functionality, including for example aromatic ketone functionality such as substituted benzophenone and derivatives thereof. The carbonyl carbon can have at least one substituted or unsubstituted aromatic ring bonded to it. In a preferred embodiment, photocrosslinkable vinyl monomers can be used. Acrylate, methacrylate, acrylamide, and methacrylamide systems are preferred embodiments. Traditional coupling reactions between, for example, hydroxyl and carboxylic acid, or amino groups and carboxylic acids can be used to form monomers having photocrosslinking groups, as well as other groups described herein including selective binding groups and energy absorbing moieties.

Benzophenone and its derivatives are preferred as they have several advantages including: chemical stability, activation at wavelengths such as 350–360 nm which avoid protein damage, preferential reaction with unreactive C—H bonds even in the presence of water and bulk nucleophiles. This group can also react with its own polymer chain or with other polymer chains at many places on the chain, not just at another photocrosslinkable group.

The first polymer preferably is crosslinked by photocrosslinking. Other methods of crosslinking can be used such as, for example, thermal crosslinking or chemical crosslinking. For example, multiple polymers can be blended together which are reactive with each other. The reaction can be controlled so that initially a high quality film is formed before inducing reaction between the polymers.

III. Second Polymer: Functional Polymer

The invention also provides a second polymer for blending with the first polymer. In a preferred embodiment, the second polymer can comprise functionality for selectively binding a biomolecular analyte, wherein the functionality for selective binding a biomolecular analyte in the first polymer and the second polymer can be the same or different. For example, the second polymer can be coupled with selective binding functionality, and the selective binding functionality can be part of second monomeric units. This coupling can occur before or after the second polymer is mixed with the first polymer. In general, the second polymer does not need to have a photocrosslinkable group although it should have functionality such as C—H bonds or other reactive groups distributed along its polymer chain which can react with the photocrosslinkable functionality of the first polymer. Functionalities for selective binding which are useful chromatography absorbents can also be used for the coating biochip applications described herein.

The second monomeric subunits that comprise a selective binding functionality for binding a biomolecular analyte, particularly protein, are not particularly limited and some examples are already described above with respect to the first polymer. Selective binding and reaction can be based on covalent or non-covalent interactions and the binding moieties can be covalent binding moieties or non-covalent binding moieties. For example, a variety of selective binding functionalities are described in U.S. patent publication No. 2002/0060290 A1 and WO 00/66265, cited above. Thus, the '290 patent publication discloses a variety of adsorbents beginning at paragraph 70 which selectively bind analytes. These include adsorbents based on salt-promoted interactions (paragraph 73), hydrophilic interaction adsorbents (paragraph 80), electrostatic interaction adsorbents (paragraph 84), coordinate covalent interaction adsorbents (paragraph 93), enzyme-active site interaction adsorbents (paragraph 98), reversible covalent interaction adsorbents (paragraph 100), glycoprotein interaction adsorbents (paragraph 102), and biospecific interaction adsorbents (paragraph 104). Other interactions include hydrophobic interactions. Combinations of interactions can be used.

Furthermore, WO 00/66265 discloses a series of selective binding functionalities, or binding functionalities, including those listed at pages 13–15.

Alternatively, the second polymer can comprise a reactive functionality for attaching a biomolecule that, itself, acts as a selective binding functionality.

Alternatively, the second polymer can comprise energy absorbing moieties that assist in desorption/ionization of analytes into the gas phase in laser desorption/ionization processes.

Functional Groups

Binding functionalities and EAM functionalities are described further.

1. Binding Functionalities

Binding functionalities generally can fall into multiple classes including the following two classes: Reactive functionalities that can form a covalent bond with the target, and adsorbent functionalities, that can form a non-covalent bond with the target.

a. Reactive Functionalities

Reactive functional groups are useful for attaching other molecules to the hydrogel. For example, one may want to attach biomolecules, such as polypeptides, nucleic acids, carbohydrates or lipids to the hydrogel. Exemplary reactive functional groups include:

(a) carboxyl derivatives such as N-hydroxysuccinimide esters, N-hydroxybenztriazole esters, acid halides, acyl imidazoles, thioesters, p-nitrophenyl esters, alkyl, alkenyl, alkynyl and aromatic esters;

(b) haloalkyl groups wherein the halide can be later displaced with a nucleophilic group such as, for example, a bromoacetyl group;

(c) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(d) sulfonyl halide groups for subsequent reaction with amines, for example, to form sulfonamides;

(e) reactive thiol groups, which can react with disulfides on proteins, including 2-mercaptopyridines and orthopyridinyl disulfides;

(f) sulfhydryl groups, which can be, for example, acylated or alkylated;

(g) alkenes, which can undergo, for example, Michael addition, etc (e.g., maleimide);

(h) epoxides, which can react with nucleophiles, for example, amines and hydroxyl compounds;

(i) hydrazine groups, which react with sugars and glycoproteins;

(j) vinyl sulfones;

(k) activated carbonyl groups.

The reactive functional groups can be chosen such that they do not participate in, or interfere with reactions in which they are not intended to participate in. Alternatively, the reactive functional group can be protected from participating in the reaction by the presence of a protecting group. Those of skill in the art will understand how to protect a particular functional group from interfering with a chosen set of reaction conditions. For examples of useful protecting groups, See, Greene et al., Protective Groups In Organic Synthesis, John Wiley & Sons, New York, 1991.

Those of skill in the art understand that the reactive functional groups discussed herein represent only a subset of functional groups that are useful in assembling the chips of the invention.

Exemplary reactive functional monomers are imidazole, phenylcarboxyethanol, N-hydroxysuccinimide, N-hydroxymaleimide, cystamine/DTT, glycidol, p-nitrophenyl methylol carbonate, benzotriazoyl methylol carbonate, $MeSCH_2CH_2OH$, Ellman's reagent (4-nitro-3-carboxylic acid)disulfide and O-pyridinyl-disulfide.

b. Adsorbent Functionalities

Binding functionalities (which also can be attached through reactive functionalities) are useful for capturing analytes from a sample for further analysis. Binding functionalities may be grouped into two classes—biospecific binding groups and chromatographic binding groups.

Binding functionalities can be chromatographic or biospecific. Chromatographic binding functionalities bind substances via charge-charge, hydrophilic-hydrophilic, hydrophobic-hydrophobic, van der Waals interactions and combinations thereof.

Biospecific binding functionalities generally involve complementary 3-dimensional structures involving one or more of the above interactions. Examples of combinations of biospecific interactions include, but are not limited to, antigens with corresponding antibody molecules, a nucleic acid sequence with its complementary sequence, effector molecules with receptor molecules, enzymes with inhibitors, sugar chain-containing compounds with lectins, an antibody molecule with another antibody molecule specific for the former antibody, receptor molecules with corresponding antibody molecules and the like combinations. Other examples of the specific binding substances include a chemically biotin-modified antibody molecule or polynucleotide with avidin, an avidin-bound antibody molecule with biotin and the like combinations. Biospecific functionalities are generally produced by attaching the biospecific moiety through a reactive moiety, as above.

In an exemplary embodiment, the binding functionality monomer includes a binding functionality that is selected the group consisting of a positively charged moiety, a negatively charged moiety, an anion exchange moiety, a cation exchange moiety, a metal ion complexing moiety, a metal complex, a polar moiety, a hydrophobic moiety. Further exemplary binding functionalities include, an amino acid, a dye, a carbohydrate, a nucleic acid, a polypeptide, a lipid (e.g., a phosphotidyl choline), and a sugar.

Ion exchange moieties of use as binding functionalities in the polymers of the invention are, e.g., diethylaminoethyl, triethylamine, sulfonate, tetraalkylammonium salts and carboxylate.

In an exemplary embodiment, the binding functionality is a polyaminocarboxylate chelating agent such as ethylenediaminetetraacetic acid (EDTA) or diethylenetriaminepentaacetic acid (DTPA), which is attached to an amine on the substrate, or spacer arm, by utilizing the commercially available dianhydride (Aldrich Chemical Co., Milwaukee, Wis.). When complexed with a metal ion, the metal chelate binds to tagged species, such as polyhistidyl-tagged proteins, which can be used to recognize and bind target species. Alternatively, the metal ion itself, or a species complexing the metal ion can be the target.

Metal ion complexing moieties include, but are not limited to N-hydroxyethylethylenediaminoe-triacetic acid (NTA), N,N-bis(carboxymethyl)-L-lysine, iminodiacetic acid, aminohydroxamic acid, salicylaldehyde, 8-hydroxy-quinoline, N,N,N'-tris(carboxytrimethyl)ethanolamine, and N-(2-pyridylmethyl)aminoacetate. The metal ion complexing agents can complex any useful metal ion, e.g., copper, iron, nickel, cobalt, gallium and zinc.

The organic functional group can be a component of a small organic molecule with the ability to specifically recognize an analyte molecule. Exemplary small organic molecules include, but are not limited to, amino acids, heparin, biotins, avidin, streptavidin carbohydrates, glutathiones, nucleotides and nucleic acids.

In another exemplary embodiment, the binding functionality is a biomolecule, e.g., a natural or synthetic peptide, antibody, nucleic acid, saccharide, lectin, member of a receptor/ligand binding pair, antigen, cell or a combination thereof. Thus, in an exemplary embodiment, the binding functionality is an antibody raised against a target or against a species that is structurally analogous to a target. In another exemplary embodiment, the binding functionality is avidin, or a derivative thereof, which binds to a biotinylated analogue of the target. In still another exemplary embodiment, the binding functionality is a nucleic acid, which binds to single- or double-stranded nucleic acid target having a sequence complementary to that of the binding functionality.

In another exemplary embodiment, the chip of this invention is an oligonucleotide array in which the binding functionality at each addressable location in the array comprises a nucleic acid having a particular nucleotide sequence. In particular, the array can comprise oligonucleotides. For example, the oligonucleotides can be selected so as to cover the sequence of a particular gene of interest. Alternatively, the array can comprise cDNA or EST sequences useful for expression profiling.

In a further embodiment, the binding functionality is selected from nucleic acid species, such as aptamers and aptazymes that recognize specific targets.

In another exemplary embodiment, the binding functionality is a drug moiety or a pharmacophore derived from a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds, which are being screened for their ability to interact with a target of choice. As such, drug moieties, which are useful in practicing the instant invention include drugs from a broad range of drug classes having a variety of pharmacological activities.

a. Exemplary hydrophobic adsorbent functional monomers include $CH_3(CH_2)_{17}OH$, 1-Octadecanol, 1-Docosanol, perfluorinated polyethyleneglycol (Sovay, USA).

Exemplary hydrophilic adsorbent functional monomers include polyvinyl alcohol) and polyvinylpyrolidone.

Exemplary anion exchange adsorbent functional monomers include 3-chloro-2-hydroxypropyl trimethylammonium chloride and 2-hydroethyl-N-methyl pyridium chloride.

Exemplary cation exchange adsorbent functional monomers include 1,4-butanediol-2-sulfonic acid, 3,5-dimethylo benzenesulfonic acid, dihydroxybenzoic acid and dimethylolacetic acid.

Exemplary metal chelate adsorbent functional monomers include N-hydroxyethylethylenediamino-triacetic acid (NTA), N,N-bis(carboxymethyl)-L-lysine, aminohydroxamic acid, salicylaldehyde, 8-hydroxy-quinoline, N,N,N'-tris(carboxytrimethyl)ethanolamine, and N-(2-pyridylmethyl)aminoacetate. The addition of a solution of metal ions, such as copper, nickel, zinc, iron and gallium functionalizes the gel.

2. EAM Functionalities

In some embodiments, EAM (energy absorbing molecule) functionalities can be useful for promoting desorption and ionization of analyte into the gas phase during laser desorption/ionization processes. The EAM monomer comprises a photo-reactive moiety as a functional group. The photo-reactive moiety preferably includes a nucleus or prosthetic group that specifically absorbs photo-radiation from a laser source. The photo-reactive groups absorbs energy from a high fluence source to generate thermal energy, and transfers the thermal energy to promote desorption and ionization of an analyte in operative contact with the gel. In the case of UV laser desorption, the EAM monomer preferably includes an aryl nucleus that electronically absorbs UV photo-irradiation. In the case of IR laser desorption, the EAM monomer preferably includes an aryl nucleus or prosthetic group which preferably absorbs the IR radiation through direct vibrational resonance or in slight off-resonance fashion. A UV photo-reactive moiety can be selected from benzoic acid (e.g., 2,5 di-hydroxybenzoic acid), cinnamic acid (e.g., α-cyano-4-hydroxycinnamic acid), acetophenone, quinone, vanillic acid, caffeic acid, nicotinic acid, sinapinic acid pyridine, ferrulic acid, 3-amino-quinoline and derivatives thereof. An IR photo-reacitve moiety can be selected from benzoic acid (e.g., 2,5 di-hydroxybenzoic acid), cinnamic acid (e.g., α-cyano-4-hydroxycinnamic acid), acetophenone (e.g. 2,4,6-trihyroxyacetophenone and 2,6 -dihyroxyacetophenone) caffeic acid, ferrulic acid, sinapinic acid 3-amino-quinoline and derivatives thereof.

IV. Blending Conditions

The blending conditions are not particularly limited and can be functionally controlled to achieve desired results as known to those skilled in the art. Polymer blending is described in, for example, *Concise Encyclopedia of Polymer Science and Engineering*, Ed. J. I. Kroschwitz (Wiley), 1990, "Polymer Blends", pages 830–835, and references cited in the bibliography including, for example, D. R. Paul et al., *Polymer Blends*, Vol. I and II, Academic Press, New York, 1978. In general, solution blending and film casting methods are preferred to provide films and layers of a desired thickness. For example, solutions can be filtered to improve quality. Drying rates can be controlled. One skilled in the art can tailor the order of the addition of the reagents, use blocking groups, and other methods known in the art to protect functional groups so that the desired functionality is achieved in the final hydrogel blend.

The amounts of the first and second polymers, and the amounts of the photocrosslinking functionality and the functionality for selective binding a biomolecular analyte provide the hydrogel precursor polymer blend composition with, respectively, the ability to be photocrosslinked into a hydrogel and the ability of the hydrogel to selectively bind to the biomolecular analyte. For example, the first polymer can comprise about 0.5 mole % to about 15 mole % monomeric subunits comprising photocrosslinkable functionality, or more particularly, about 1 mole % to about 7 mole % monomeric subunits.

The weight percentage of the first polymer can be, for example, about 5 wt. % to about 60 wt. %, and more particularly, about 15 wt. % to about 45 wt. %. The weight percentage of the second polymer can be, for example, about 40 wt. % to about 95 wt. %, and more particularly, about 55 wt. % to about 85 wt. %. However, if for example the first and second polymer is used together with a diluent polymer such as, for example, unmodified dextran, the weight percentage of the second polymer can be, for example, about 25 wt. % to about 80 wt. %, and more particularly, about 40 wt. % to about 60 wt. %. Particular working examples are described below, and the amounts of the first and second polymers, the amounts of the photocrosslinking functionality, and the amounts of the functionality for selective binding can be further controlled for particular applications.

Molecular weight is another parameter which can be controlled for achieving desired blend properties including solution viscosity and ability to form high quality coatings. For example, the first polymer and the second polymer each can have weight average molecular weight of about 1,000 to about 10,000,000, and more particularly, about 10,000 to about 1,000,000, and more particularly about 20,000 to about 100,000.

In addition to the first and second polymers, blending agents can be used including, for example, fluorescently modified polymers or polymers modified with fluorescent groups as noted above with respect to FIG. 1. In general, polymer modified blending agents are preferred which have the same polymer backbone as the first and second polymers. For example, for a dextran-based first and second polymer, fluorescently modified dextran can be used such as, for example, fluorescein dextran. Dextran can be modified or conjugated with fluorescent indicators such as fluorophores, dyes, and the like and such products are commercially available or can be custom synthesized. Fluroescent groups can be selected which are compatible with the photocrosslinking group. For example, absorption and emission spectra can be used to select a suitable fluorescent polymer.

Another type of blending agent is to use a polymer which has the same polymer backbone as the first and second polymers but is not modified to have a functionality which selectively binds to biomolecular analytes or which are photocrosslinkable. These blending agents can be a diluent to the functional groups and provide for better control of crosslinking and binding density.

V. Methodology for Functionalizing a Surface and Manufacturing a Substrate

In order to functionalize a surface with hydrogel blend according to the present invention, a four step approach can be used. In one step, a support surface can be prepared, optionally with a primer layer. In another step, the polymeric hydrogel blend precursor can be prepared in bulk. In still another step, the bulk polymeric hydrogel blend precursor can be physically attached to the surface substrate as a uniform polymeric coating. Finally, photocrosslinking conditions can be applied such as, for example, exposure to UV light, to form the hydrogel surface coating, induce surface binding and/or fixation, and generate polymer networking.

To functionalize a surface with hydrogel, the polymeric hydrogel precursor can be first dissolved or suspended in a single or mixed solvent system. The solvent system can be aqueous or organic. The solvent system can be partially or completely removed before use of photocrosslinking conditions. The polymeric hydrogel precursor can be then contacted with the surface to form a layer on the surface.

The method of layering and forming films of the polymeric hydrogel precursor onto the substrate surface is not particularly limited. To achieve a uniform layering, for example, methods can be used including spin coating, dip coating, roll coating, spraying, screen printing, inkjet printing, chemical vapor deposition, and other known coating methods. The coating process can be applied to an individual chip substrate. Alternatively, the individual chip substrate can be assembled into the fixture of large surface area to where the coating process can be applied. In another embodiment, the convention semiconductor process can be used: the coating solution can be applied to large flat surface to form uniform coating, and the coated wafer then can be cut into many small pieces with appropriate dimension. The diced piece can be used as a chip directly or be transferred and mounted on the chip carrier substrates. Wafer materials can be, for example, plastic, glass, silicon, metal, or metal oxide. Uniformity in the hydrogel surface coating may provide a more accurate time-of-flight analysis of samples, as all analytes absorbed on the probe surface are equidistant from an energy source of a gas phase ion spectrometer. The copolymeric hydrogel precursor, as compared to a monomer solution used for deposition and in situ polymerization and cross-linking, is of sufficient viscosity which makes the deposition hydrogel layer more compatible with established coating processes, which facilitates the formation of uniform and consistent hydrogel surfaces.

The polymeric hydrogel precursor can be coated onto the surface either in the form of discontinuous discrete spots or continuous layers. Known patterning methods including photolithography and masks can be used.

The photopolymerization can be regionally controlled with use of photomasks to generate patterns, as known in the art. Areas which are not exposed to light can be washed away, leaving the crosslinked hydrogel. These can be in the form of spots. For example, spots can be generated with a lateral dimension that is about 100 nm to about 3 mm, and more particularly, about 500 nm to about 500 microns.

Substrates are generally described in WO 00/66265, pages 15–17. The substrate can be made of any suitable material that is capable of supporting hydrogel material. The substrate can have various properties including porous or non-porous, rigid or flexible. The substrate surface can be in any shape including planar. However, the substrate with a flat surface would better provide the uniform polymeric coating.

Composite or multi-component substrates can be used such as, for example, two-component substrates. In a two-component substrate, for example, a solid piece of silicon or glass can be inserted in an aluminum frame-holder. A long strip can be machined out of the aluminum substrate to accommodate the glass slide or silicon wafer insert. An adhesive can be used for attachment.

Coating on aluminum substrate is a particularly preferred embodiment.

The substrate surface can be physically or chemically modified to improve adhesion of the hydrogel blend to the substrate. In chemical modification, for example, the substrate surface can be the surface of a primer layer that is supported by a support layer. The primer layer is not particularly limited but can be, for example, a hydrophobic primer layer. A hydrophobic primer layer is preferred, as it also can function as a passivation layer to protect the substrate surface from aqueous solution. It can be, for example, a silane primer layer, a hydrocarbon silane primer layer, a fluorinated silane primer layer, a mixed fluorinated/hydrocarbon silane primer layer, or a polymeric primer layer. When oxide substrates are used, alkoxysilane and chlorosilane chemistry can be used to form the primer layer. When noble metal substrates are used such as, for example, gold and silver, then alkanethiols or disulfides can be used to form the primer layer.

Examples of physical modification of the substrate surface include conditioning to make the surface rough, microporous, or porous.

The thickness of the primer layer is not particularly limited but can be, for example, about 4 angstroms to about 10 microns, and more particularly, about 5 nm to about 10 microns, and more particularly, about 10 nm to about 10 microns.

The type of support layer is not particularly limited but can be organic or inorganic. It can be, for example, aluminum, silicon, glass, metal oxide, metal, polymer, or composite. When the hydrogel is used as a SELDI probe, conductive supports can be used. Plastic materials can be used as supports. Characteristics of plastic materials can be further changed by combining or blending different types of polymers together and by adding other materials. For instance, particulate fillers such as, for example, carbon powder, silica, ceramic, and powdered metals can be incorporated to adjust the modulus and electrical conductivity of the composite. Other additives can be used to improve chemical resistance and thermal stability.

The substrate surface, whether primed or not, can be tailored with the photocrosslinkable functionality to allow a photochemical fixation of hydrogel coating. For example, benzophenone-types of photocrosslinkable functionality can bind with C—H groups. The substrate surface can comprise photoreactive functionality to facilitate binding with the hydrogel during photocrosslinking.

The photocrosslinking can be selective such that some of the polymeric hydrogel precursor is photocrosslinked and some of the polymeric hydrogel precursor is not. Discreet spots of crosslinked hydrogel can be formed. The remainder can be removed by, for example, washing in water. The result is a patterned surface. Traditional photolithographic methods including photomasks can be used. If the substrate surface is hydrophobic, the areas between the hydrophilic hydrogel can be hydrophobic. Hence, liquid drops of aqueous solution can be retained on a specific spot.

In a preferred embodiment, the polymeric hydrogel precursor that is crosslinked is a substantially uniform layer on the substrate surface and has an average layer thickness of about 5 nm to about 50 microns, and more particularly, about 5 nm to about 10 microns, and more particularly, about 10 nm to about 10 microns, and more particularly about 100 nm to about 10 microns, and more particularly, about 100 nm to about 2 microns.

The thickness of these hydrogel coatings can be an important aspect of the invention. The thickness of the hydrogel coatings is typically estimated by methods known in the art, e.g., with the combined measurements of reflectometry and reflectance FTIR. Thickness can be, for example, about 1 micron to about 10 microns, and more particularly, about 2 microns to about 5 microns.

The present invention is not limited by theory, but a relatively thick hydrogel coating can provide probe surface with more surface area and higher number of binding functional groups available for sample capturing. Hence, a higher binding capacity would be expected. However, in the process of SELDI, it is important for the bound proteins to be extracted out of the hydrogel layers and co-crystallized with EAM before being desorbed and ionized by laser excitation. It may be difficult for thick hydrogel to completely release the captured analytes in a simple extraction step, and thin hydrogel layers may thus enable the extraction and use of the captured analytes more efficiently.

Therefore, the thickness of hydrogel coatings affects not only the binding capacity, but also the extraction efficiency. The optimal thickness would be achieved by balancing of binding capacity and extraction efficiency.

The substrate can be a substrate for a biochip. In this regard, the hydrogel can be covalently bound to the substrate surface.

VI. Using a Blended Hydrogel:

One or more kits can be prepared for using the hydrogel blends according to the invention. For example, in one embodiment, a hydrogel coating kit is provided comprising: (a) a first composition comprising a first polymer comprising a photocrosslinkable functionality, wherein the first polymer optionally also comprises functionality for selectively binding a biomolecular analyte, and (b) a second composition comprising a second polymer comprising (i) functionality for selectively binding a biomolecular analyte, wherein the functionality for selective binding a biomolecular analyte in the first polymer and the second polymer can be the same or different, or (ii) one or more energy absorbing moieties. The two components can be packaged in separate containers and sold with instructions concerning, for example, the contents of the kits and directions for mixing the components including the amounts of the components. The instructions can further describe the types of biomolecular analytes which the compositions can selectively bind for. If desired, substrates can be provided with the kits include substrates for mass spectral analysis. With the kits, biochips can be prepared.

In another kit, a hydrogel coating kit comprises: (a) a first composition comprising a first polymer comprising a photocrosslinkable functionality, wherein the first polymer optionally also comprises functionality for selectively binding a biomolecular analyte, and (b) a second composition comprising a second polymer which can be synthetically modified to comprise functionality for selectively binding a biomolecular analyte. Additional reagents can be provided for synthetically modifying the second polymer to comprise functionality for selective binding the biomolecular analyte. Again, instructions can be provided.

Biochips coated with the blended hydrogels of this invention can be used to detect analytes applied to the gel by any methods known in the art. When the hydrogel is functionalized with a binding group, the chip will capture onto the surface analytes that bind to the particular group. Unbound materials can be washed off. Analytes can be detected by any suitable method including a gas phase ion spectrometry method, an optical method, an electrochemical method, atomic force microscopy and a radio frequency method. Gas phase ion spectrometry methods include, e.g., mass spectrometry, ion mobility spectrometry, and total ion current measuring. Optical methods include microscopy (both confocal and non-confocal), imaging methods and non-imaging methods. Optical detection can involve detection of fluorescence, luminescence, chemiluminescence, absorbance, reflectance, transmittance, and birefringence or refractive index (e.g., surface plasmon resonance ("SPR"), ellipsometry, quartz crystal microbalance, a resonant mirror method, a grating coupler waveguide method (e.g., wavelength interrogated optical system ("WIOS")) and interferometry). Electrochemical methods include, e.g., voltametry and amperometry techniques. Radio frequency methods include, e.g., multipolar resonance spectroscopy. Some of these methods can detect real-time binding events between an analyte and a capture molecule. Others, such as laser desorption mass spectrometry involve a surface-based analytical tool (SBAT) that requires direct physical communication with the surface of the substrate on which the analyte is captured.

The samples are not particularly limited but can contain a biological fluid that is selected from fluids such as saliva, sputum, blood, serum, urine, lymphatic fluid, prostatic fluid, seminal fluid, milk, a cell extract, cell culture medium and derivatives thereof. In some embodiments, the sample can be pre-fractionated by size exclusion chromatography and/or ion exchange chromatography before contact with the adsorbent surface.

The sample can be contacted with the hydrogel adsorbent on the probe substrate. The treatment at this point depends upon the method of detection. For example, in the case of SELDI, the sample can be allowed to dry on the hydrogel adsorbent. This can result in both specific and nonspecific adsorption of the analytes in the sample by the hydrogel adsorbent, without washing away analytes that are not bound to the hydrogel adsorbent. Generally, a volume of sample containing from a few attomoles to 100 picomoles of analyte in about 1 microliter to about 500 microliters is sufficient for binding to the hydrogel adsorbent.

After the liquid sample has been removed, in certain embodiments, an energy absorbing material can be applied to the probe. Examples of energy absorbing materials include, but are not limited to, a cinnamic acid derivative, sinapinic acid, and dihydroxybenzoic acid.

After the analyte is applied to the probe and dried, it is detected using gas phase ion spectrometry. Analytes or other substances bound to the adsorbents on the probes can be analyzed using a gas phase ion spectrometer. The quantity and characteristics of the analyte can be determined using gas phase ion spectrometry. Other substances in addition to the analyte of interest can also be detected by gas phase ion spectrometry, e.g., laser desorption ionization mass spectrometry.

Gas Phase Ion Spectrometry Detection:

Data generation in mass spectrometry begins with the detection of ions by an ion detector. A typical laser desorption mass spectrometer can employ a nitrogen laser at 337.1 nm. A useful pulse width is about 4 nanoseconds. Generally, power output of about 1–25µJ is used. Ions that strike the detector generate an electric potential that is digitized by a high speed time-array recording device that digitally captures the analog signal. Ciphergen's ProteinChip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

A computer can transform the resulting spectrum into various formats for displaying. In one format, referred to as "spectrum view or retentate map," a standard spectral view can be displayed, wherein the view depicts the quantity of analyte reaching the detector at each particular molecular weight. In another format, referred to as "peak map," only the peak height and mass information are retained from the spectrum view, yielding a cleaner image and enabling analytes with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique analytes and analytes which are up- or down-regulated between samples.

Analysis generally involves the identification of peaks in the spectrum that represent signal from an analyte. Peak selection can, of course, be done by eye. However, software is available as part of Ciphergen's ProteinChip® software that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

The spectra that are generated in embodiments of the invention can be classified using a pattern recognition process that uses a classification model. In general, the spectra will represent samples from at least two different groups for which a classification algorithm is sought. For example, the groups can be pathological v. non-pathological (e.g., cancer v. non-cancer), drug responder v. drug non-responder, toxic response v. non-toxic response, progressor to disease state v. non-progressor to disease state, phenotypic condition present v. phenotypic condition absent.

In some embodiments, data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as backpropagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are in U.S. Pat. No. 6,675,104.

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

The classification models can be formed on and used on any suitable digital computer. Suitable digital computers include micro, mini, or large computers using any standard or specialized operating system such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

Finally, the invention also includes particles and beads comprising the polymeric hydrogel precursors and hydrogels described above. An average diameter or size of the particles can be, for example, about 0.01 microns to about 1,000 microns, more particularly about 0.1 microns to about 100 microns, and more particularly, about 1 micron to about 10 microns. To provide consistent mass resolutions and intensities, the particles are preferably uniform in size or diameter. For example, the particles can have a coefficient of diameter variation of less than about 5%, preferably less than about 3%, more preferably less than about 1%. In one embodiment, the particles can be made of hydrogel, and the particle is substantially free of non-hydrogel material. In another embodiment, the particles can be made on non-hydrogel particles which are coated with hydrogel.

WORKING EXAMPLES

The invention is further described with use of the following non-limiting examples.

1. Photocrosslinkable Sax Copolymer Blends

Example 1

Summary

In a first series of experiments, a series of photocrosslinkable SAX copolymer blends were prepared by blending of 10 mol. % benzophenone (BP)-modified poly(3-(methacryloylamino)propyl trimethylammonium chloride) copolymer with poly(3-(methacryloylamino)propyl trimethylammonium chloride) homopolymer. The blended copolymers have BP molar fraction varied from 1 to 10 mol. %. In addition, 3 mol. % of benzophenone-modified SAX copolymer was also prepared by copolymerization method and used to produce hydrogel coating for comparison study.

Experiment 1

Preparation of 2-(methacryloyloxy)ethyl](4-benzoylbenzyl)dimethylammonium bromide Monomer (Photocrosslinkable Monomer)

Figure 2:
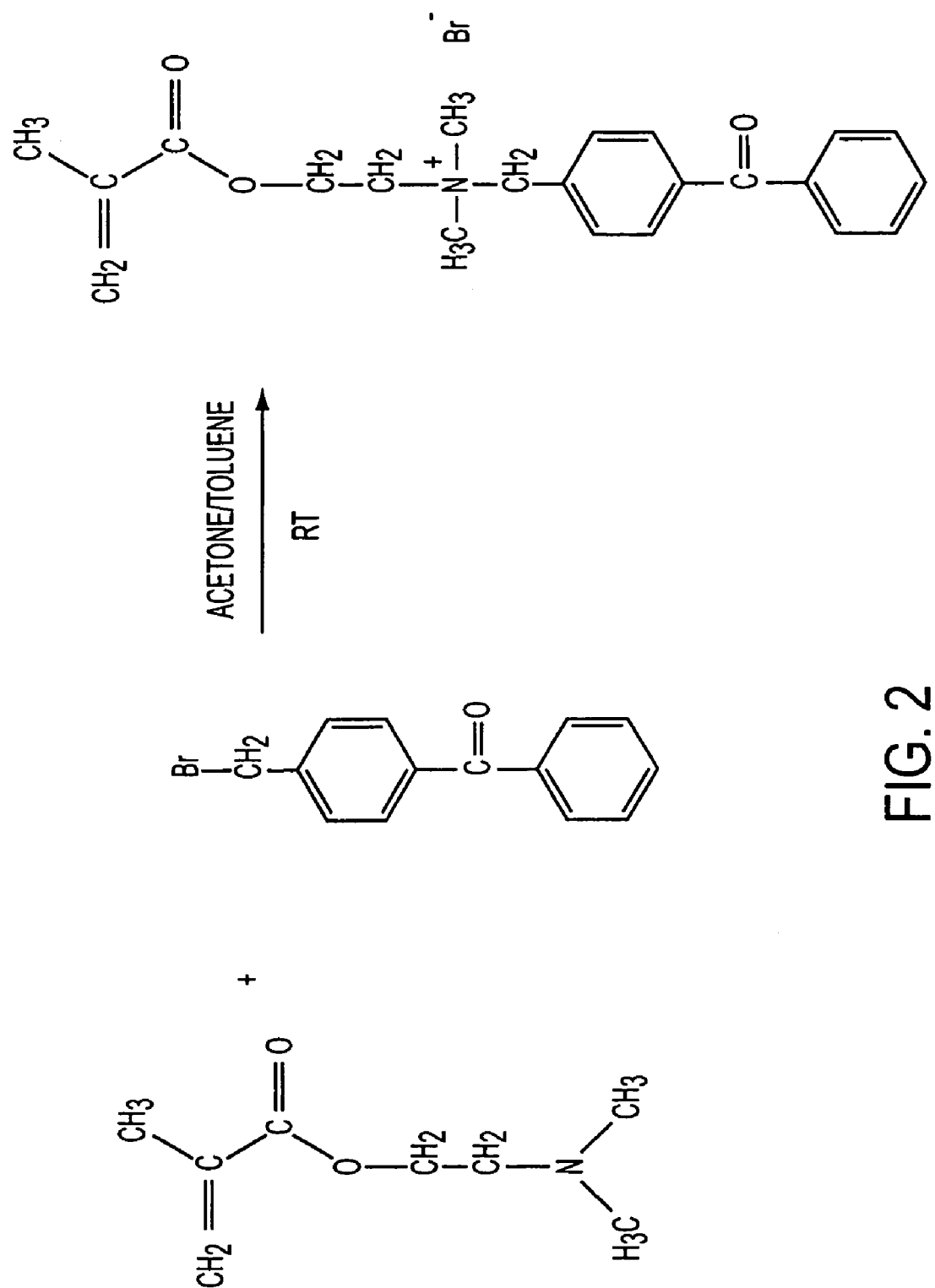
FIG. 2. Synthesis of 2-(Methacryloyloxy)ethyl](4-benzoylbenzyl) Dimethylammonium Bromide Monomer.

In accordance with FIG. 2, 132 mL of toluene/acetone (5:1, v/v) were added to a dry, 250-mL round bottom flask, equipped with a magnetic stirrer, along with 15.45 grams of 4-(bromomethyl)benzophenone (Aldrich). To this solution, 10.59 grams of 2-(dimethylamino)ethyl methacrylate in 20 ml of toluene were added dropwise at room temperature. After 2 hours, the precipitates were filtered and washed with acetone four times. The product powders were then dried under vacuum. The yield is about 90%. $^1$H NMR confirmed the formation of the desired product.

Experiment 2

Preparation of Copolymer of 3-(methacryloylamino)propyl trimethylammonium chloride (SAX) Monomer and 2-(methacryloyloxy)ethyl](4-benzoylbenzyl)dimethylammonium bromide Monomer.

Figure 3:
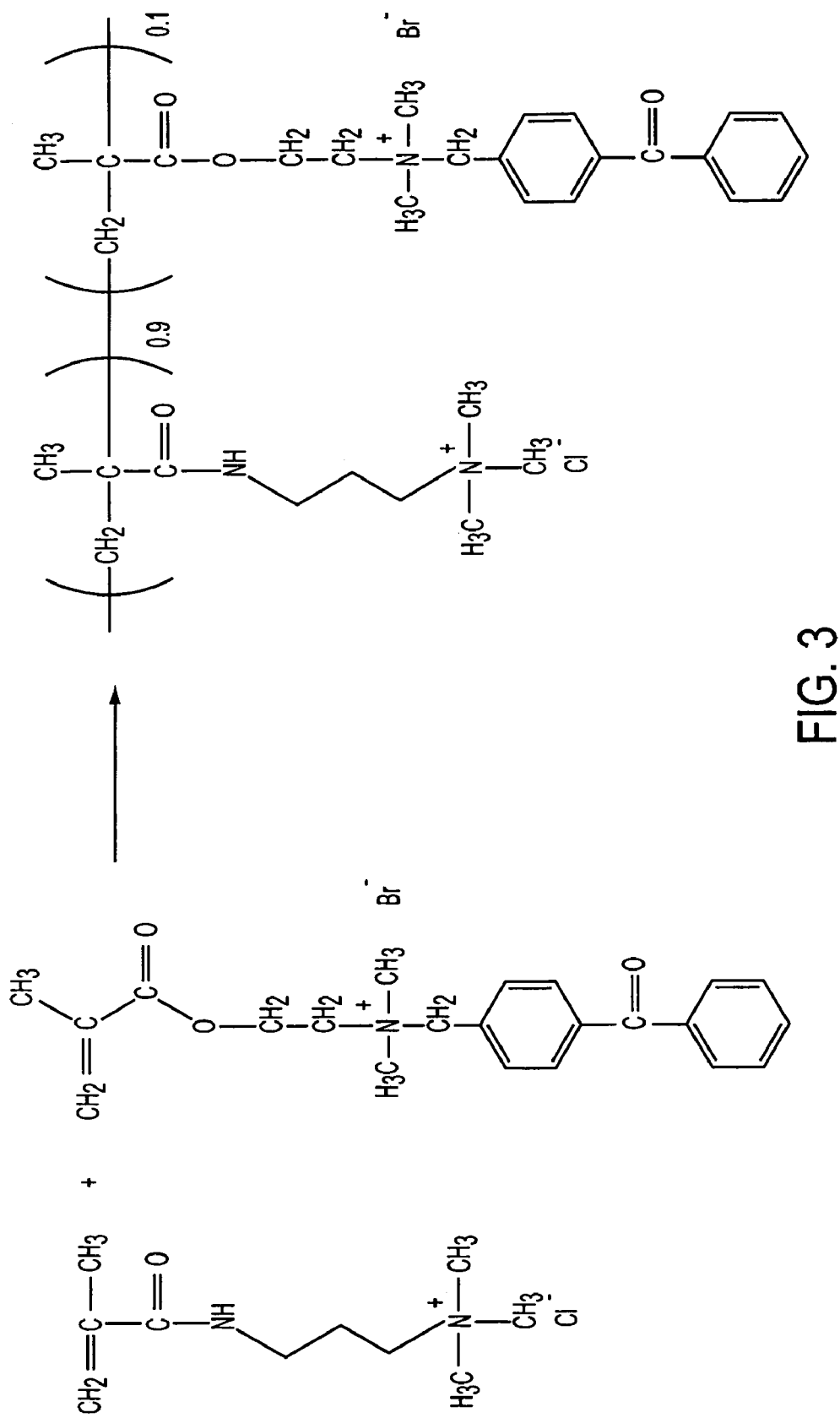
FIG. 3. Preparation of Copolymer of SAX Monomer and Photocrosslinkable Monomer.

A SAX photocrosslinkable copolymer having 10 mol. % of 2-(methacryloyloxy)ethyl](4-benzoylbenzyl)dimethylammonium bromide was prepared. As shown in FIG. 3, 44.0 grams of 3-(methacryloylamino)propyl-trimethylammonium chloride solution (Aldrich, 50 wt. % in water) were mixed with 60 grams of distilled water, followed with 4.79 grams of 2-(methacryloyloxy)ethyl](4-benzoylbenzyl)dimethylammonium bromide, and 0.36 grams of V-50 (Wako Chemical), a water-soluble, cationic azo-initiator. The solution was purged with a flow of argon for five minutes. The vessel was sealed and then heated at 58° C. for 40 hours. The solution became very viscous after polymerization. The polymer solution was diluted with DI water and freeze-dried under vacuum to obtain a white solid of the product.

Experiment 3

Preparation of Homo-Polymers of 3-(methacryloylamino)propyl trimethylammonium chloride (SAX).

180.0 grams of 3-(methacryloylamino)propyl-trimethylammonium chloride solution (Aldrich, 50 wt. % in water) were mixed with 400 grams of distilled water, followed with 0.17 grams of V-50 (Wako Chemical), a water-soluble, cationic azo-initiator. The solution was purged with a flow of argon for five minutes. The vessel was sealed and then heated at 58° C. for 40 hours. The solution became very viscous after polymerization. The polymer solution was diluted with DI water and freeze-dried under vacuum to obtain a white solid of the product.

Experiment 4

Preparation of 3 mol. % BP-Modified SAX Copolymers by Blending.

1.665 grams of 10 mol. % benzophenone-modified SAX copolymer were mixed with 3.886 grams of SAX homopolymer in 37 mL of DI $H_2O$/2-isopropanol (7/3, w/w), and a clear solution was obtained. The solution was filtered and used for coating experiments. The same procedure was applied to prepare blended copolymers having 1 mol. % BP-modified SAX copolymers.

Experiment 5

Preparation of 3 mol. % BP-Modified SAX Copolymers by Copolymerization 3 mol. % BP-modified SAX copolymer was also prepared by copolymerization for comparison study.

70 grams of 3-(methacryloylamino)propyl-trimethylammonium chloride solution (Aldrich, 50 wt. % in water) were mixed with 93 grams of distilled water, followed with 2.04 grams of 2-(methacryloyloxy)ethyl](4-benzoylbenzyl)dimethylammonium bromide and 0.30 grams of V-50 (Wako Chemical), a water-soluble, cationic azo-initiator. The solution was purged with a flow of argon for five minutes. The vessel was sealed and then heated at 58° C. for 40 hours. The solution became very viscous after polymerization. The polymer solution was diluted with DI water and freeze-dried under vacuum to obtain a white solid of the product.

Experiment 6

Preparation of SAX Hydrogel Coatings on $SiO_2$-Coated Aluminum Substrates

The blended copolymers solution having 3 mol. % of photocrosslinkable groups were dispensed on the surface of methacrylate-coated aluminum substrates. The substrates then were subjected to a process of spin-coating at 3,000 RPM for one minute. The polymer-coated chips then were exposed for 20 minutes to UV light of approximately 360 nm in wavelength (Hg short arc Lamp, 20 mW/cm$^2$ at 365 nm). FTIR results confirmed the formation of SAX hydrogel coating on the surface of aluminum substrates.

For comparison study, 3 mol. % BP-modified SAX copolymers prepared by copolymerization were also used for hydrogel formation.

To check the stability of SAX hydrogel coatings on the surface of aluminum substrates, SAX polymeric hydrogel-coated chips were immersed in DI water, and surface reflectance FTIR was used to follow this experiment. FTIR spectra showed, in all the cases, that there was no decrease in IR peak intensity of hydrogel coatings after water immersions for several hours. The results demonstrated that the hydrogel coatings prepared from the blended copolymers are as stable as that from copolymerization. Therefore, the blending approach provides route to adjust the average BP content, without the need to do a separate polymerization run to make each specific copolymer for tuning the optimal BP content.

Figure 4A:
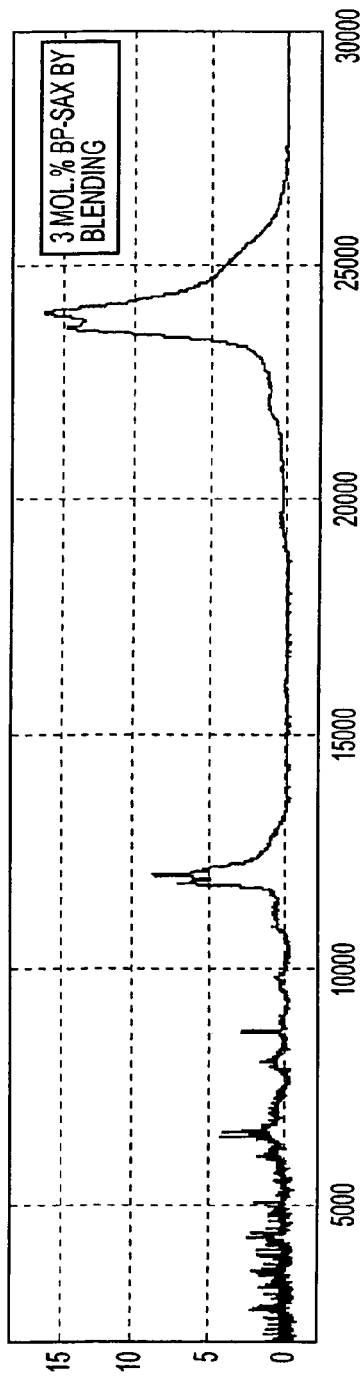
FIGS. 4A and 4B. Serum Profiling of SAX Chip Prepared by Blending.
Figure 4B:
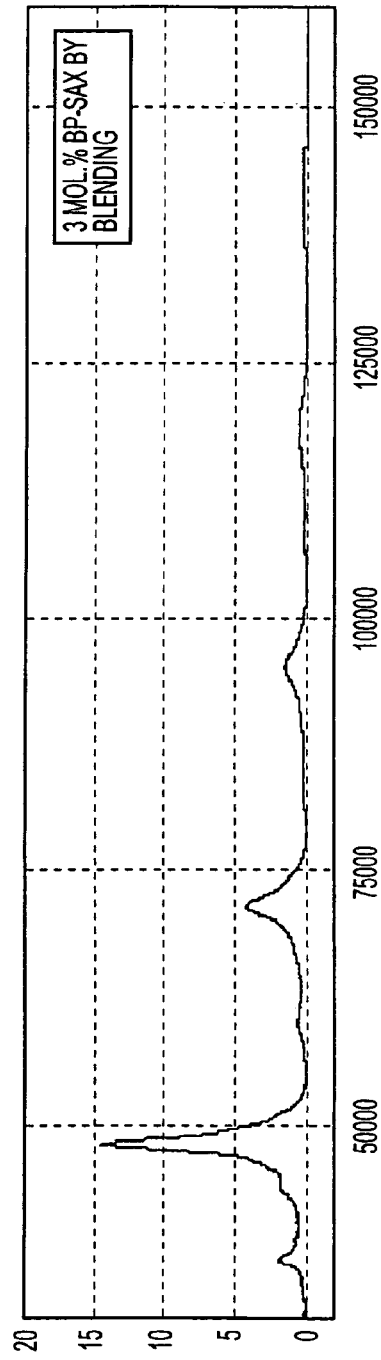

In the context of SELDI analysis, moreover, the SAX chips prepared with blending method and with copolymerization method have essentially identical features. Both strongly bound milk protein sample in 50 mM pH 9.0 Tris-HCl buffer solution. For protocols of using ProteinChip, see, for example, WO 00/66265 (Rich et al., "Probes for a Gas Phase Ion Spectrometer," Nov. 9, 2000). FIGS. 4A and 4B show the composite mass spectrum of the SAX chips prepared with blending method at low and high molecular mass of protein recognition profile. The profile shows the proteins retained on the SAX probe.

2. Dextran-Based Materials.

Experiment 7

Derivatization of Dextran with 4-benzoylbenzoic acid.

Figure 5:
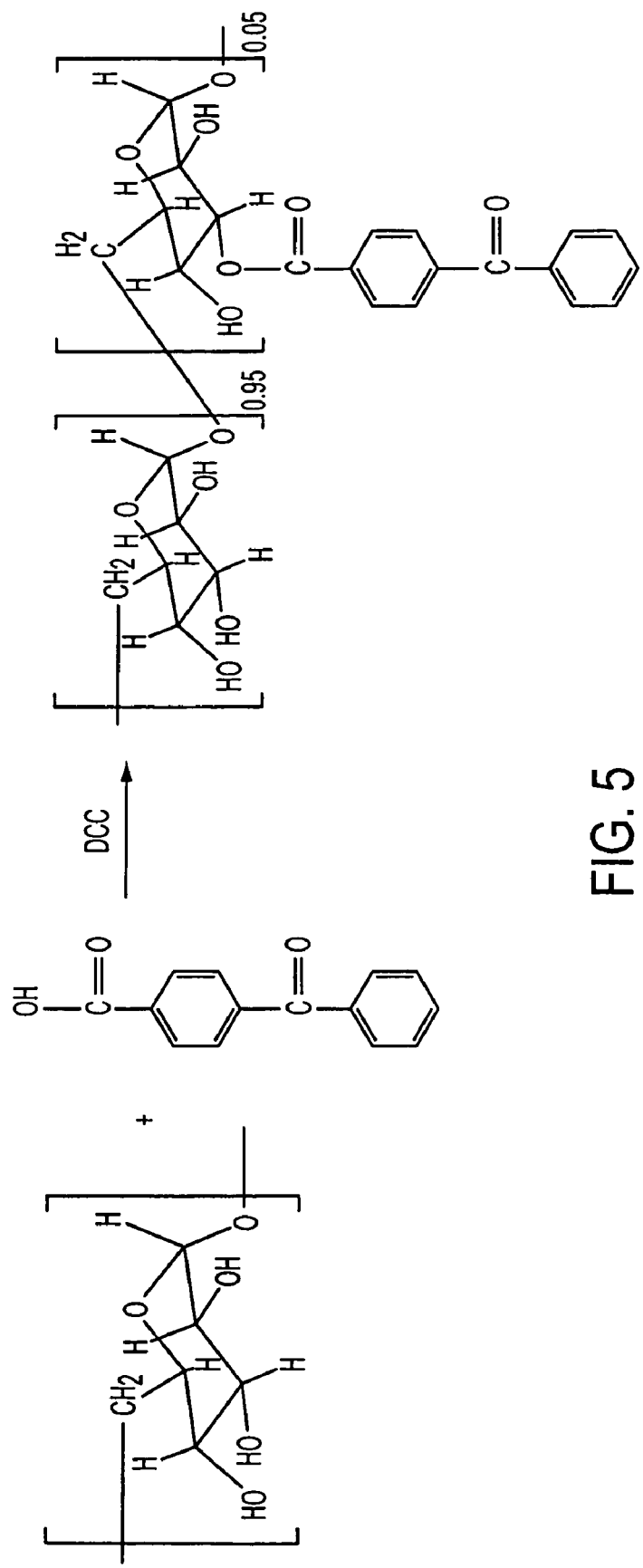
FIG. 5. Reaction of Dextran with 4-Benzoylbenzoic acid.

As shown in FIG. 5, 4-benzoylbenzoic acid is reacted with dextran by using 1,3-dicyclohexylcarbodiimide (DCC) as a coupling reagent to prepare BP-modified dextran. The synthetic procedure is as follows:

300 mL of DMSO were added to a dry, 500-mL round bottom flask, equipped with a magnetic stirrer, along with 17.54 grams of dextran (MW about 70,000, Sigma; vacuum dried at 100° C. overnight before use)), 8.57 grams of 4-benzoylbenzoic acid, 11.72 grams of 1,3-dicyclohexylcarbodiimide (DCC), and 6.94 grams of dimethyaminopyridine. The solution was cooled with an ice bath and stirred for 1 h. The ice bath was removed and the solution was stirred at room temperature overnight. After then, the precipitated by-product was filtered off, the filtrate was poured into acetone to precipitate the polymer. The polymer precipitates were re-dissolved in DI water, and the solution mixture was dialyzed against DI water through a seamless cellulose tube (cutoff molecular weight, 12,000). The dialyzed polymer solution was freeze-dried under vacuum, yielding a white solid of the product. $^1$H NMR confirmed the formation of the desired product. The modification degree is ~5 mol. % (one out of 20 sugar units was modified with a BP unit).

Derivatization of Dextran with 4-(glycidyloxy)benzophenone.

An alternative approach to BP-modified dextran is by reacting 4-(glycidyloxy)benzophenone with dextran.

Experiment 8

Synthesis of 4-(glycidyloxy)benzophenone

Figure 6:
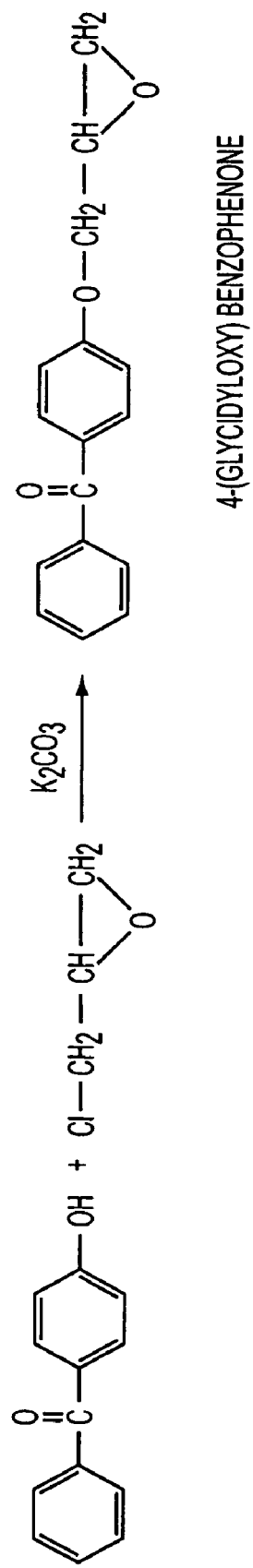
FIG. 6. Synthesis of 4-(Glycidyloxy)benzophenone.

As illustrated in FIG. 6, 100 mL of dried acetone were added to a dry, 250-mL round bottom flask, equipped with a magnetic stirrer, along with 15.05 grams of 4-hydroxybenzophenone, 32.1 grams of epichlorohydrin, and 6.2 grams of potassium carbonate. The solution was heated to reflux for 6 hours and then cooled to room temperature. The precipitated potassium chloride was filtered off, and the solution was evaporated to remove excess epichlorohydrin. The crude product was recrystallized from methanol. $^1$H NMR data confirmed the formation of the desired product.

Experiment 9

Reaction of Dextran with 4-(glycidyloxy)benzophenone.

Figure 7:
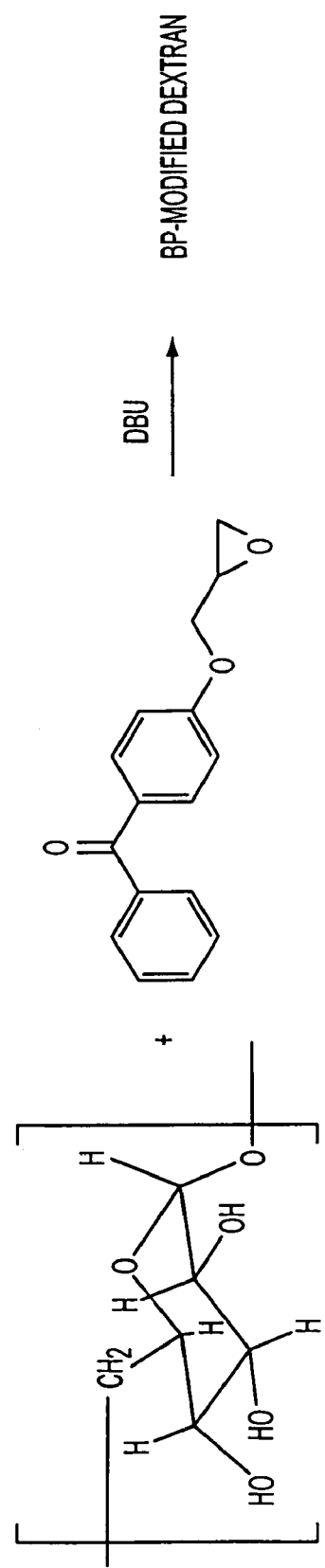
FIG. 7. Reaction of Dextran with 4-(Glycidyloxy)benzophenone.

In accordance with FIG. 7, 100 mL of DMSO were added to a dry, 250-mL round bottom flask, equipped with a magnetic stirrer, along with 23.85 grams of dextran (MW about 70,000, Sigma; Vacuum dried at 100° C. overnight before use)), 6.04 grams of 4-(glycidyloxy)benzophenone, and 3.96 grams of 1,8-diazabicyclo[5.4.0]undec-7-ene (DBU). The solution was stirred at room temperature overnight. After then, the solution was poured into acetone to precipitate the polymer. The polymer precipitates were re-dissolved in DI water, and the solution mixture was dialyzed against DI water through a seamless cellulose tube (cutoff molecular weight, 12,000). The dialyzed polymer solution was freeze-dried under vacuum, yielding a white solid of the product. $^1$H NMR confirmed the formation of the desired product. The modification degree is about 3 mol. %.

Experiment 10

Preparation of 1,1'-Carbonyldiimidazole (CDI)-Preactivated Dextran Chips

Preparation of BP-Modified Dextran Solution by Blending.

One part of 5 mol. % BP modified-dextran are mixed with one part of native dextran (MW about 70,000, Sigma) in DI water/isopropanol solvent mixture to afford 2.5 mol. % BP modified blended dextran solution.

1 mol. % BP-modified blended dextran solution was also prepared by blending one part of 5 mol. % BP modified-dextran with four parts of native dextran (MW about 70,000, Sigma) in DI water/isopropanol solvent mixture.

The concentration of BP is correlated with the swelling properties of the hydrogel coatings, which impacts important parameters such as the structure, mechanical properties, and permeability of surface-attached networks.

Experiment 11

Preparation of Dextran Hydrogel Coatings on Al Surface

Figure 8:
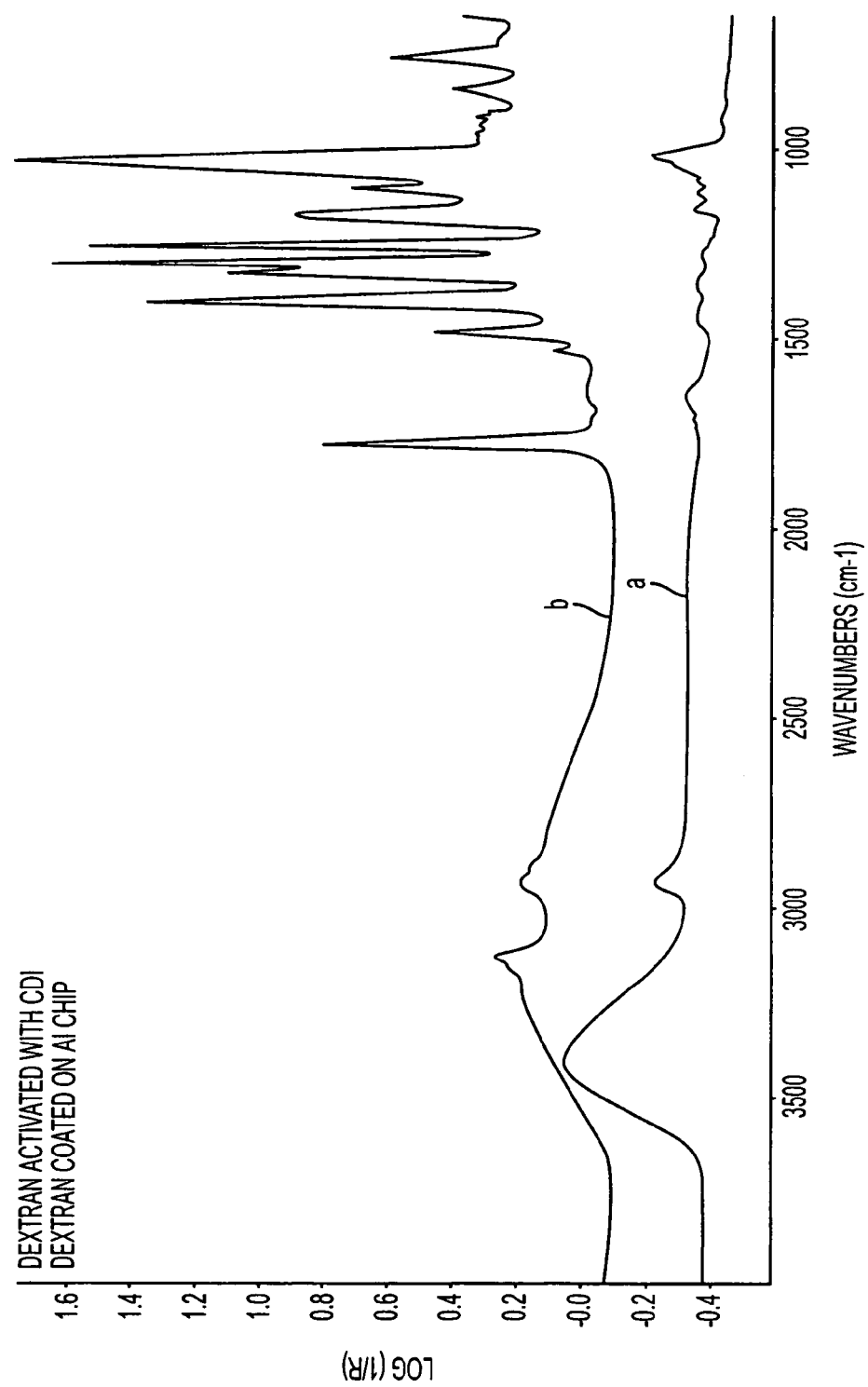
FIG. 8. Reflectance FTIR Spectra of (a) Dextran Hydrogel; (b) CDI-activated Dextran Hydrogel on Al chip.

The blended dextran solution with 2.5 mol. % BP content was dispensed on the surface of methacrylate-coated aluminum substrates, the substrates were subjected to a process of spin-coating at 3,000 RPM for one minute. The polymer-coated chips then were exposed for 20 minutes to UV light of approximately 360 nm in wavelength (Hg short arc Lamp, 20 mW/cm$^2$ at 365 nm). Reflectance FTIR results (see FIG. 8(a)) confirmed the formation of dextran hydrogel coating on the surface of aluminum substrates. The obtained coating was stable against water-immersion for 24 h.

The dextran-coated chip was reacted with 1,1'-carbonyldiimidazole (CDI, Aldrich) to prepare pre-activated surface. The synthetic procedure was as follows:

The dextran-coated chips were immersed into a 5 wt. % solution of carbonyldiimidazole (CDI) in DMSO for one hour. The chips then were removed from the solution and washed with DMSO followed with acetone, dried with a flow of nitrogen. Reflectance FTIR spectrum (see FIG. 8(b)) confirmed nearly quantitative conversion of the hydroxyl groups to the imidazole carboxylic ester, as indicated by the nearly complete disappearance of the hydroxyl peak (3500–3300 cm$^{-1}$) and the formation of a strong carbonyl peak at 1771 cm$^{-1}$.

Figure 9:
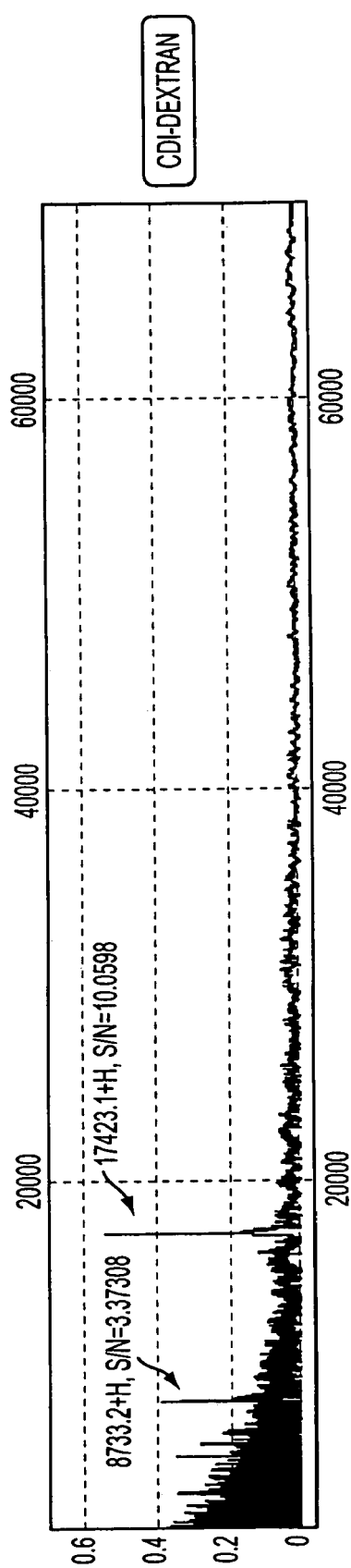
FIG. 9. SELDI Spectrum of CDI-Dextran Chip Used for an Antibody-Antigen Recognition Study.

These CDI-activated chips are designed to covalently bind with free primary amine groups. Typical applications include immunoassays, receptor-ligand binding studies and transcription factor analysis. For protocols of using Protein-Chip, see, for example, WO 00/66265 (Rich et al., "Probes for a Gas Phase Ion Spectrometer," Nov. 9, 2000). FIG. 9 shows the SELDI spectrum of a typical antibody-antigen recognition profile. The SELDI results indicated that the CDI-dextran chips provide good specific-binding and a lower level of non-specific binding.

Experiment 12

Preparation of Diethylaminoethyl-Dextran (DEAE-Dextran) Chips

Preparation of BP-Modified DEAE Dextran Solution by Blending 38.4 mg of DEAE Dextran (MW>500,000, Aldrich) are mixed with 9.6 mg of 5 mol. % BP-modified dextran to afford 1 mol. % BP DEAE dextran blended solution.

To prepared DEAE hydrogel coatings, 3 wt. % of the above solution was dispensed on the surface of methacrylate-coated aluminum substrates, After being dried, the polymer-coated chips then were exposed for 20 minutes to UV light of approximately 360 nm in wavelength (Hg short arc Lamp, 20 mW/cm$^2$ at 365 nm). Reflectance FTIR results confirmed the formation of DEAE dextran hydrogel coating on the surface of aluminum substrates.

To evaluate the chemical stability of the hydrogel coating, DEAE chips were immersed into the various solvent systems, reflectance FTIR was then used to check the retention of the chemistry on the surface. Four kinds of solvent conditions were used: DI water, 0.2M NaCl buffer, acetonitrile, and DMSO. The chips were immersed in the solvents for a period of 2–20 h at RT. Reflectance FTIR was used to check the chemistry change before and after the solvent-immersion. The IR results showed that the DEAE hydrogels are stable to 0.2M NaCl buffer, acetonitrile, and DMSO up to 20 h-immersion. The hydrogel is also stable to DI water up to 4 h-immersion.

Figure 10A:
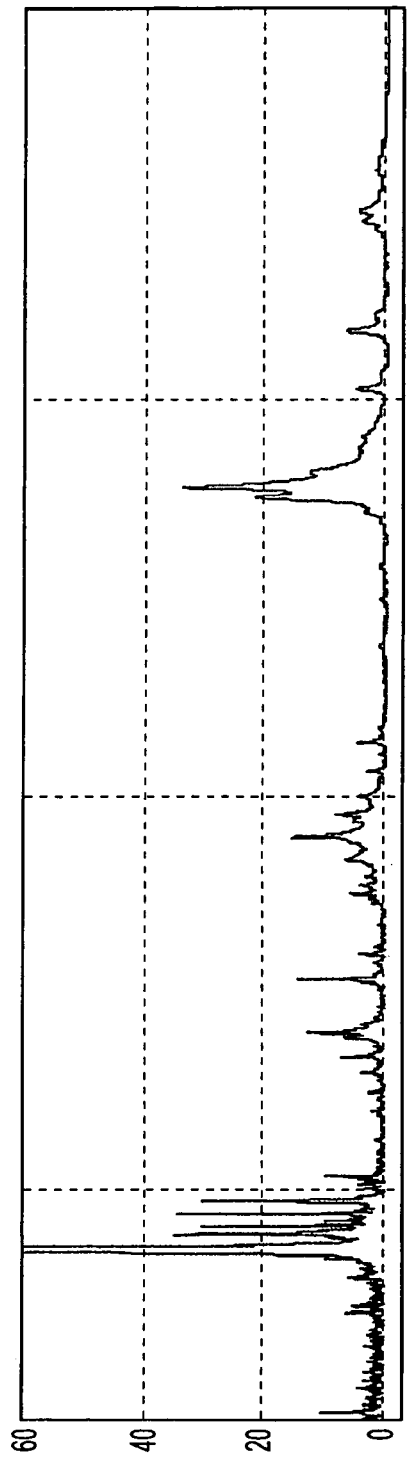
FIGS. 10A and 10B. Serum Profiling of DEAE Dextran Chip Prepared by Blending.
Figure 10B:
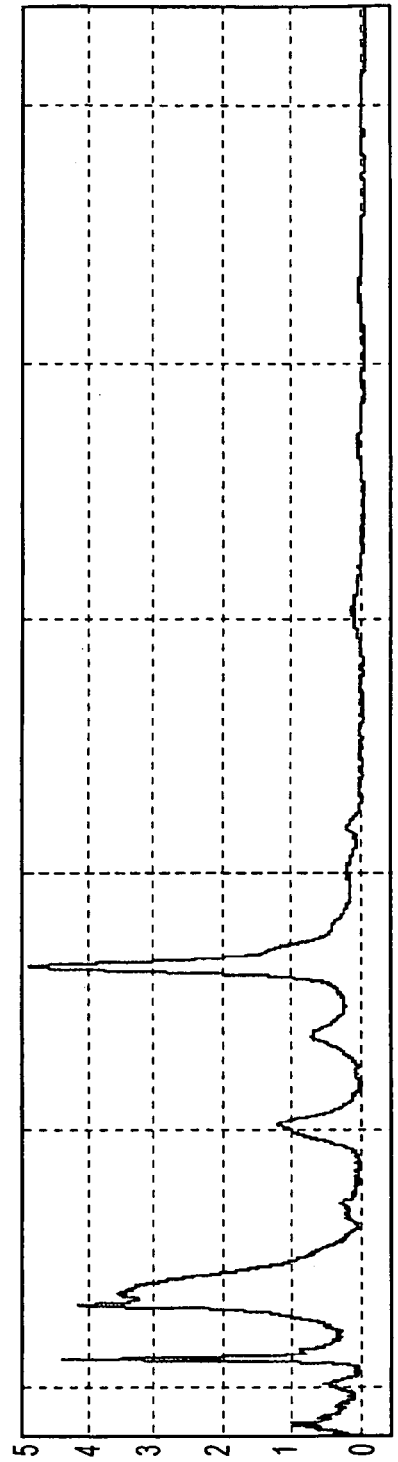
Figure 11A:
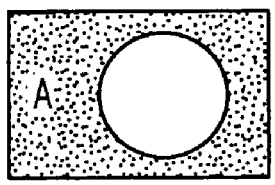
FIGS. 11A and 11B. MEP Dyed with Ponceau S.
Figure 11B:
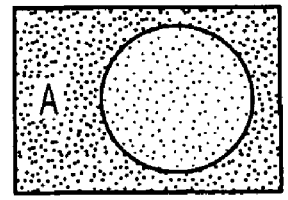
Figure 12A:
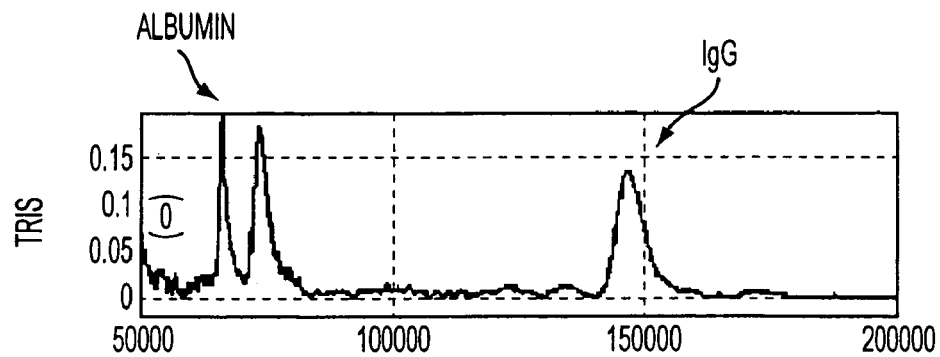
FIGS. 12A, 12B and 12C. Selective binding/washing of IgG on MEP
Figure 12B:
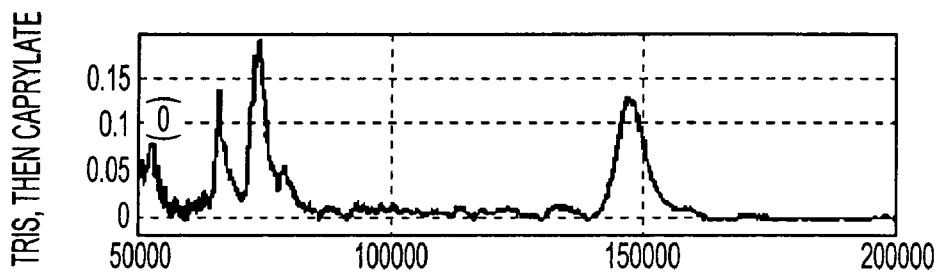
Figure 12C:
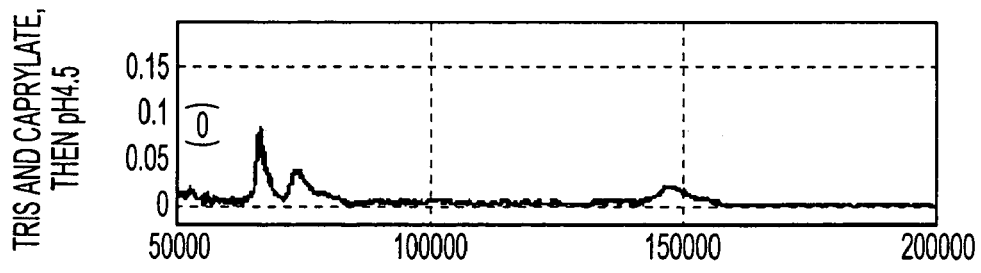
Figure 13A:
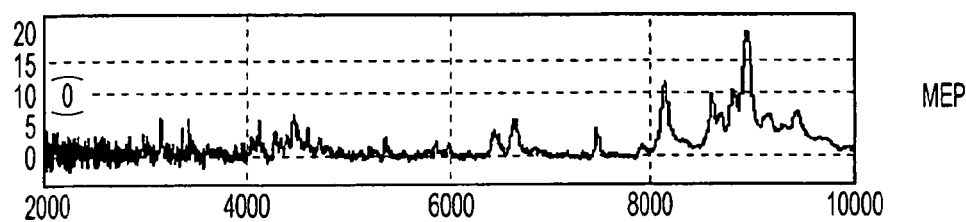
FIGS. 13A, 13B and 13C. Profiling of Albumin Depleted Serum
Figure 13B:
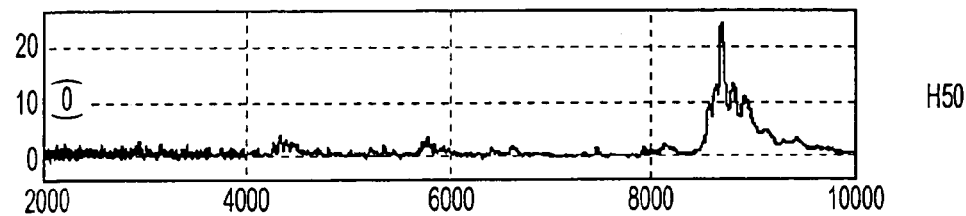
Figure 13C:
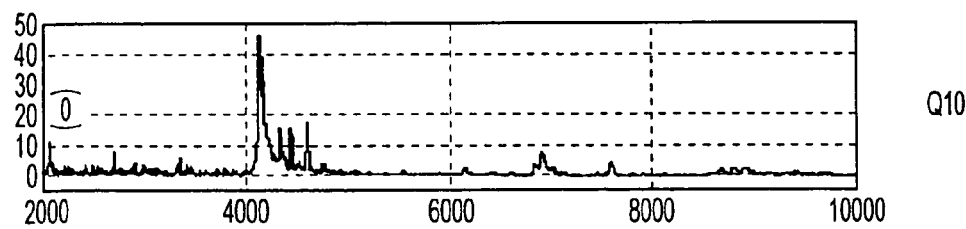
Figure 14A:
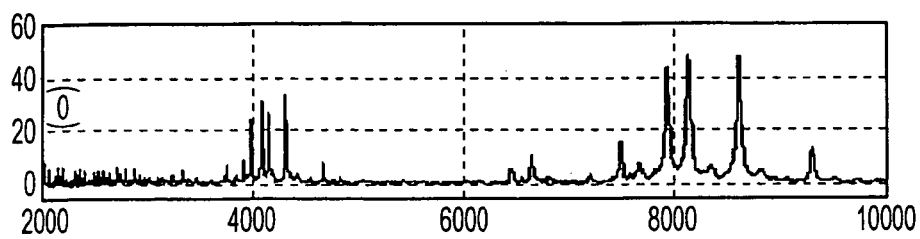
FIGS. 14A, 14B and 14C. Profiling of Albumin Depleted Serum
Figure 14B:
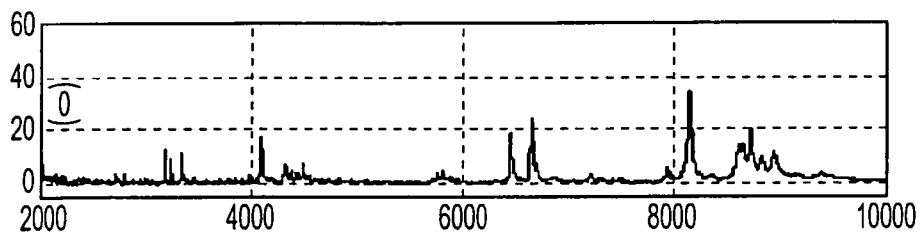
Figure 14C:
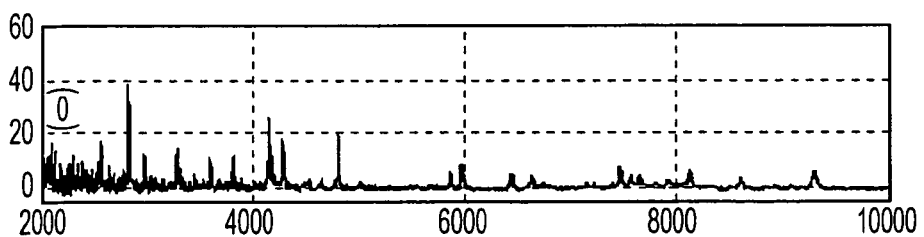
Figure 15A:
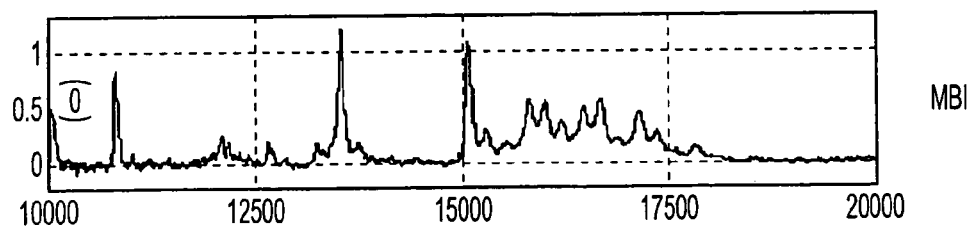
FIGS. 15A, 15B and 15C. Profiling of Albumin Depleted Serum
Figure 15B:
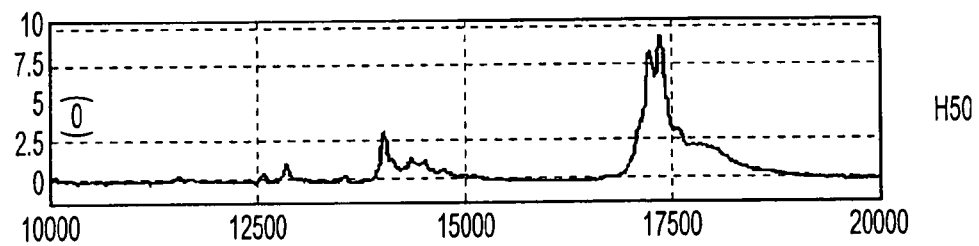
Figure 15C:
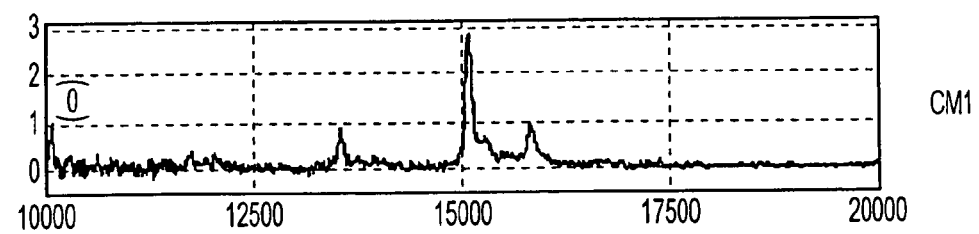

In the context of SELDI analysis, moreover, the DEAE dextran chips strongly bound albumin depleted human serum in 50 mM pH 7.5 Tris-HCl buffer solution. For protocols of using ProteinChip, see, for example, WO 00/66265 (Rich et al., "Probes for a Gas Phase Ion Spectrometer," Nov. 9, 2000). FIGS. 10A and 10B show the composite mass spectrum at low and high molecular mass of albumin depleted human serum protein recognition profile. The profile shows the serum proteins retained on the DEAE dextran probe.

Experiment 13

Preparation of Dextran Sulphate Chips

Dextran sulphate sodium salt is a polyanionic derivative of dextran.

Preparation of BP-Modified Dextran Sulphate Solution by Blending.

12.8 mg of dextran sulphate (MW>500,000, Aldrich), 25.6 mg of native dextran (MW 500,000, Aldrich) are mixed with 9.6 mg of 5 mol. % BP-modified dextran to afford 1 mol. % BP blended dextran sulphate in aqueous solution. Native dextran was used as diluent to adjust the density of the binding functionalities.

To prepared dextran sulphate hydrogel coatings, 3 wt. % of the above solution was dispensed on the surface of methacrylate-coated aluminum substrates, After being dried, the polymer-coated chips then were exposed for 20 minutes to UV light of approximately 360 m in wavelength (Hg short arc Lamp, 20 mW/cm$^2$ at 365 nm). Reflectance FTIR study confirmed the formation of dextran sulphate hydrogel coatings on the surface of aluminum substrates.

Experiment 14

Protocol to Prepare MEP/MBI Chip Array

Substrate Preparation:
   A flat aluminum substrate was coated with Silicon Dioxide, then with methacryloxypropyl-trimethoxy silane using CVD (chemical vapor deposition)
Benzophenone-modified Dextran: See Experiment 7.
Dextran Modification: MEP
   Allylation, then MEP modification
      Allylation
         20 g of Dextran (Sigma, MW ~70,000) was dissolved in 100 ml of DI water.
         200 mg of Sodium Borohydride was added to prevent oxidation.
         Then 12.5 ml of Sodium Hydroxide was added.
         After 5 min, 2 ml of Allylbromide was added.
         After 16 hrs with stirring, the product (allyl-dextran) was precipitated out with 200 ml of acetone.
         For the purification, the solid was redissolved in 100 ml of water, then pour 200 ml of acetone. Repeat this one more time.
         Finally, the solid was redissolved in 200 ml of DI water, then freeze dried.
      MEP Modification
         This allylated dextran (2 g) was dissolved in 20 ml of DI water.
         1.0 g of Mercaptoethylpyridine-HCl (Biosepra) and 20 mg of AZAP (2,2'-Azobis (2-methylpropionamide)dihydrochloride) were added to this solution sequentially.
         Then the solution was purged with argon then capped.
         The solution was kept at 85° C. for 2 hr with agitation.
         The product was precipitated out with 50 ml of acetone, then redissolved in 20 ml of DI water.
         The product was further purified by dialysis using MWCO 5000 cellulose membrane, then freeze dried
Dextran Modification: MBI
   Allylation, Bromination, then MBI modification
      Allylation
         10 g of Dextran (Sigma, MW ~70,000) was dissolved in 50 ml of DI water.
         100 mg of Sodium Borohydride was added to prevent oxidation.
         Then 12.5 ml of Sodium Hydroxide was added.
         After 5 min, 3 ml of Allylbromide was added.
         After 16 hrs with stirring, the product (allyl-dextran) was precipitated out with 100 ml of acetone.
         For the purification, the solid was redissolved in 50 ml of water, then pour 100 ml of acetone. Repeat this one more time.
         Finally, the solid was redissolved in 200 ml of DI water, then freeze dried.
      Bromination
         This allylated dextran (5 g) was dissolved in 100 ml of DI water.
         1.5 g of N-Bromosuccinimide (Aldrich) and 2.5 g of Potassium Bromide were added to this solution sequentially.

Then the pH was adjusted between 3.7 and 3.9 with Phosphoric Acid (diluted ⅓ with DI water).

The solution was stirred for one hour at room temperature under the hood (because of bromine generation).

MBI Modification 2.7 g of Mercaptobenzimidazole sulfonic acid (Aldrich) was added to the solution pH was adjusted between 11 and 11.5 with 10M NaOH pH was checked for one hour and adjusted, if necessary After 16 hrs, 200 ml of acetone was added to the solution to precipitate out the product Product was dissolve with 100 ml of water, then dialysed with MWCO 5,000 Cellulose Dialysis bag The product (MBI-dextran) was obtained as a white powder after freeze dry Benzophenone-modified Dextran: see experiment 7

Coating of MEP/MBI Polymer onto the Substrate:

2% of modified dextran solutions were made in DI water

Make a working solutions

For MEP 900 ul of 2% MEP-Dextran, 100 ul of 2% Benzophenone-Dextran, 400 ul of 10% Glycerol, and 100 ul DI water were added into a 4 ml amber vial.

For MBI Arrays 900 ul of 2% MBI-Dextran and 100 ul of 2% Benzophenone-Dextran were added into a 4 ml amber vial.

1 µl of dextran solution above and 1 µl of ethanol were deposited onto the silanated substrate sequentially The surface was dried in the oven, and irradiated for 20 min with a near UV exposure to cure Following the irradiation, the surface was washed with DI water and dried The following working example was previously described in U.S. patent application Ser. No. 10/660,738 filed Sep. 12, 2003 and noted above in description of Embodiment A.

Experiment 15 Preparation of an MBISA Biochip Array

Substrate Preparation

A flat aluminum substrate ("the chip") was coated via sputtering with Silicon Dioxide. A hydrophobic polymer (Cytonix, Beltsville, Md.) was applied to create addressable locations on the chip. Chips prepared in this manner were cleaned in a plasma cleaner and introduced into a chemical vapor deposition (CVD) oven. Methacryloxypropyl-trimethoxy silane was deposited via CVD onto the chips, a vacuum was applied, and the coated chips then cured at 60° C.

Dextran Modification

Allylation 10 g of Dextran (Sigma, MW ~75,000) was dissolved in 50 ml of deionized water, together with 100 mg of Sodium Borohydride to prevent oxidation. Sodium hydroxide solution (12.5 ml) was added to the dextran mixture, followed after 5 minutes by the addition of allylbromide (3 mL). After 16 hrs with stirring, the product (allyl-dextran) was precipitated by the addition of 100 mL of acetone. The allylated dextrose was purified by twice precipitating the crude product from water solutions (50 mL) by the addition of acetone (100 mL). Finally, the purified product was redissolved in 200 ml of DI water, then freeze dried.

Bromination and Mercaptobenzimidazole Sulfonic Acid Modification

A water solution (100 mL) of allylated dextran (5 g) was treated sequentially with 1.5 g of N-Bromosuccinimide (Aldrich) and 2.5 g of Potassium Bromide. Then the pH was adjusted between 3.7 and 3.9 with Phosphoric Acid (diluted ⅓ with DI water). The resultant solution was stirred for one hour at room temperature (under a fume hood because of bromine generation).

2.7 of mercaptobenzimidazole sulfonic acid (Aldrich) was added to the solution. The pH was adjusted between 11 and 11.5 with 10M NaOH (aq), checked for one hour, and adjusted if necessary. After 16 hrs, 200 mL of acetone were added to the solution to precipitate the crude product, which was subsequently redissolved in 100 mL of water, then dialysed with MWCO 5,000 Cellulose Dialysis bag. The resultant product (MBI-dextran) was obtained as a white powder after freeze drying.

Benzophenone Dextran

In a 250 ml round bottom flask were added 2.26 g of 4-benzoylbenzoic acid (Aldrich, Benzophenone 4-carboxylic acid), 2.26 g of Dicyclohexylcarbodiimide (Aldrich, DCC) and 50 mL of dry DMSO.

A solution of 8.1 g of Dextran (Sigma, MW ~75,000) and 0.12 g of dimethylaminopyridine (DMAP) in 100 ml of DMSO was added dropwise to the stirred benzophenone solution through an addition funnel. After stirring 16 hr, the resultant precipitate was filtered, then the solvent from the filtrate was removed on a rotary evaporator. In some instances, the crude product can be further purified by recrystallization.

Coating of MBI Polymer onto the Substrate 1.35 g of MBI dextran and 0.15 g of Benzophenone dextran as prepared above were dissolved in 100 mL of DI water. 1 µl of this dextran solution and 1 µl of ethanol were deposited sequentially onto the silanated chip. The coated chip was dried in an oven and irradiated (near UV) for 20 min. to cure. Following the irradiation, the chip was washed with DI water and dried.

Although the present invention has been described and illustrated with respect to preferred embodiments and a preferred use thereof, it is not to be so limited since modifications and changes can be made therein which are within the full scope of the invention as set forth in the appended claims.

What is claimed is:

1. A device that comprises a substrate comprising a surface that is coated with a crosslinked hydrogel polymer blend composition, wherein the composition comprises:

(i) a plurality of first polysaccharide polymer molecules, and (ii) a plurality of second polysaccharide polymer molecules, wherein the second polymer molecules are different from the first polysaccharide polymer molecules and comprise a selective binding functionality, and wherein (a) the first polysaccharide polymer molecules are photocrosslinked with each other and further photocrosslinked with the second polysaccharide polymer molecules through reacted benzophenone groups, wherein photocrosslinking results from photo-reacting benzophenone groups attached to the first polysaccharide polymer molecules, and (b) wherein the device is a probe for a mass spectrometer.

2. The device according to claim 1, wherein the first and second polysaccharide polymer molecules comprise dextran.

3. The device according to claim 1, wherein the selective binding functionality is selected the group consisting of a positively charged moiety, a negatively charged moiety, an anion exchange moiety, a cation exchange moiety, a metal ion complexing moiety, a metal complex, a polar moiety and a hydrophobic moiety.

4. The device according to claim 1, wherein the selective binding functionality is a biospecific binding functionality.

5. The device according to claim 4, wherein the biospecific binding functionality is selected from the group consisting of antibodies, receptor proteins and nucleic acids.

6. The device according to claim 1, wherein the selective binding functionality comprises a group for covalently binding a molecule.

7. The device according to claim 6, wherein the selective binding functionality is an epoxide or a carbodiimidizole.

8. The device according to claim 1, wherein the selective binding functionality is bound to an analyte selected from the group consisting of polypeptides, nucleic acids, carbohydrates and lipids.

9. The device according to claim 1, wherein the hydrogel polymer blend composition is covalently bound to the surface.

10. The device according to claim 1, wherein the hydrogel polymer blend composition is physically attached to the surface.

11. The device according to claim 1, wherein the hydrogel polymer blend composition is a film having a film thickness of about one micron to about 10 microns.

12. The device according to claim 1, wherein the substrate comprises plastic.

13. The device according to claim 1, wherein the substrate comprises a primer layer that comprises a silane, a hydrocarbon silane, a fluorinated silane, a mixed fluorinated/hydrocarbon silane, a polymer, an alkoxysilane, a chlorosilane, an alkanethiol or a disulfide.

14. The device according to claim 1, wherein the substrate comprises plastic, glass, silicon, metal, or metal oxide.

15. The device according to claim 1, wherein the hydrogel is a uniform layer on the surface.

16. The device according to claim 1, wherein the hydrogel is in the form of discrete spots on the surface.

17. The device according to claim 1, wherein the hydrogel polymer blend composition further comprises an energy absorbing moiety.

18. The device according to any of claims 1, 2, 3–8 and 9–16, wherein a matrix for laser desorption/ionization mass spectrometry is applied to the crosslinked hydrogel polymer blend composition.

19. The device according to claim 18, wherein the first polysaccharide molecules are further photocrosslinked with the surface of the substrate through reacted benzophenone groups.

20. The device according to claims 1, 2, 3–8 and 9–16, 17, wherein the first polysaccharide molecules are further photocrosslinked with the surface of the substrate through reacted benzophenone groups.

* * * * *